US011719707B2

(12) United States Patent
Clark et al.

(10) Patent No.: US 11,719,707 B2
(45) Date of Patent: Aug. 8, 2023

(54) METHODS FOR THE DIAGNOSIS AND TREATMENT OF ENDOMETRIOSIS

(71) Applicant: McMaster University, Hamilton (CA)

(72) Inventors: David Alexander Clark, Burlington (CA); Warren George Foster, Ancaster (CA)

(73) Assignee: McMaster University, Hamilton (CA)

( * ) Notice: Subject to any disclaimer, the term of this patent is extended or adjusted under 35 U.S.C. 154(b) by 428 days.

(21) Appl. No.: 16/863,023

(22) Filed: Apr. 30, 2020

(65) Prior Publication Data
US 2020/0363429 A1 Nov. 19, 2020

Related U.S. Application Data

(63) Continuation-in-part of application No. PCT/CA2018/051378, filed on Oct. 30, 2018.

(60) Provisional application No. 62/598,529, filed on Dec. 14, 2017, provisional application No. 62/578,785, filed on Oct. 30, 2017.

(51) Int. Cl.
*G01N 33/68* (2006.01)
*G01N 33/563* (2006.01)

(52) U.S. Cl.
CPC ....... *G01N 33/6893* (2013.01); *G01N 33/563* (2013.01); *G01N 2333/705* (2013.01)

(58) Field of Classification Search
USPC .......................................... 435/7.1, 329, 330
See application file for complete search history.

(56) References Cited

U.S. PATENT DOCUMENTS

| 6,955,811 B2 | 10/2005 | Gorczynski et al. |
| 7,902,151 B2 | 3/2011 | Gorczynski et al. |
| 2002/0168364 A1 | 11/2002 | Gorczynski et al. |

FOREIGN PATENT DOCUMENTS

| WO | WO-0242332 A2 * | 5/2002 | ....... C07K 14/70503 |
| WO | WO-2009121162 A1 * | 10/2009 | ........... G01N 33/566 |
| WO | 2017079335 | 5/2017 | |

OTHER PUBLICATIONS

Characteristics of multipotent mesenchymal stromal cells isolated from human endometrium and endometriosis lesions (Year: 2016).*
Kretz-Rommel A, Qin F, Dakappagari N, Cofiell R, Faas SJ, Bowdish KS. Blockade of CD200 in the presence or absence of antibody effector function: implications for anti-CD200 therapy. J Immunol (2008) 180:699-705. doi: 10.4049/jimmunol.180.2.699.
Chen, Dang-Xiao, Hao He, and Reg M. Gorczynski. "Synthetic peptides from the N-terminal regions of CD200 and CD200R1 modulate immunosuppressive and anti-inflammatory effects of CD200-CD200R1 interaction." International immunology 17.3 (2005): 289-296.

(Continued)

*Primary Examiner* — Christopher L Chin
*Assistant Examiner* — Estifanos Hailu
(74) *Attorney, Agent, or Firm* — Gowling WLG (Canada) LLP

(57) ABSTRACT

The present invention relates to methods of detecting CD200L in a female subject from a secretory phase biological sample. Increased levels of CD200L have been determined to be associated with endometriosis. CD200L is therefore a useful biomarker for the diagnosis of endometriosis and a useful target for therapeutic intervention.

5 Claims, 21 Drawing Sheets

Specification includes a Sequence Listing.

(56) References Cited

OTHER PUBLICATIONS

Gorczynski, Reginald M.: "CD200:CD200R-Mediated Regulation of Immunity", International Scholarly Research Network ISRN Immunology, vol. 2012, Article ID 682168, pp. 1-18. (APP).

Oguejiofor, Chike F., et al. "Global transcriptomic profiling of bovine endometrial immune response in vitro. I. Effect of lipopolysaccharide on innate immunity." Biology of reproduction 93.4 (2015): 100-1.

Chen, Zhiqi, et al. "Identification of an expressed truncated form of CD200, CD200tr, which is a physiologic antagonist of CD200-induced suppression." Transplantation 86.8 (2008): 1116-1124.

Clark, David A., et al. "Soluble CD200 in secretory phase endometriosis endometrial venules may explain endometriosis pathophysiology and provide a novel treatment target." Journal of Reproductive Immunology 129 (2018): 59-67.

PCT Search Report for PCT/CA2018/051378.

Mahadevan et al.—"First-In-Human Phase I Dose Escalation Study of a Humanized Anti-CD200 Antibody (Samalizumab) In Patients with Advanced Stage B Cell Chronic Lymphocytic Leukemia (B-CLL) or Multiple Myeloma (MM)". 52nd Annual Meeting of the American Society of Hematology. Orlando, Florida, Dec. 2010. Poster presentation.

\* cited by examiner

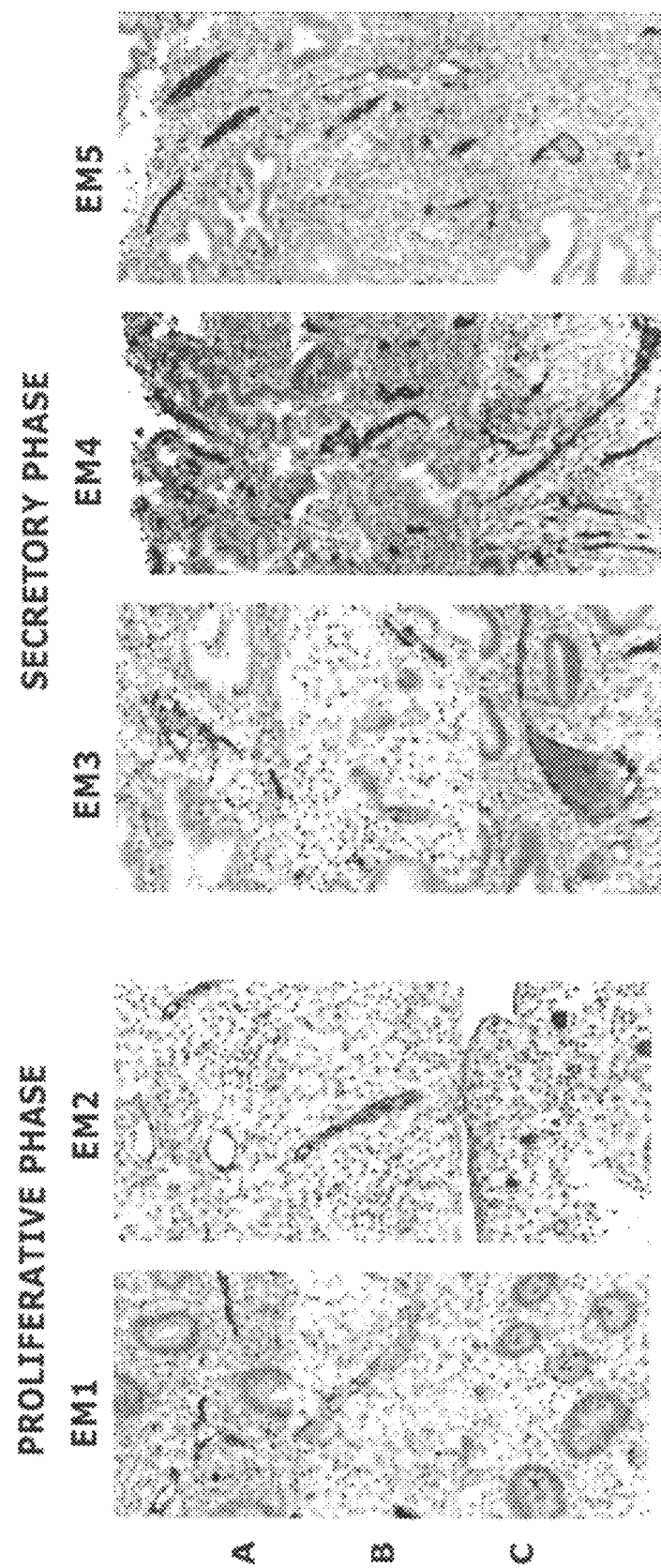
FIGURE 6, cont'd

ELISA ASSAY of sCD200 IN PERIPHERAL VENOUS BLOOD SERUM OF ENDOMETRIOSIS PATIENTS (EM) and CONTROL WOMEN (NE) DURING MENSTRUAL PHASE OF CYCLE STD = pg/ml of sCD200:Fc control antigen

```
           10         20         30         40         50
    MERLVIRMPF SHLSTYSLVW VMAAVVLCTA Q..VQVVTQDER EQLYTPASLK
           60         70         80         90        100
    CSLQNAQEAL IVTWQKKKAV SPENMVTFSE NHGVVIQPAY KDKINITQLG
          110        120        130        140        150
    LQNSTITFWN ITLEDEGCYM CLFNTFGFGK ISGTACLTVY V..QPIVSLHYK
          160        170        180        190        200
    FSEDHLNITC SATARPAPMV FWKVPRSGIE NSTVTLSHPN GTTSVTSILH
          210        220        230        240        250
    IKDPKNQVGK EVICQVLHLG TVTDFKQTVN KGYWFSVPLL LSIVSLVILL
          260        270
    VLISILLYWK RHRNQDRGEL SQGVQKMT    Exon 2 starts (¦¦) and encodes amino acids 45-95.
    (SEQ ID NO: 9)                   Exon 3 starts (¦¦¦) and encodes amino acids 170-220.
```

B)

```
           10         20         30         40         50
    MERLVIRMPF SHLSTYSLVW VMAAVVLCTA QVQVVTQDER EQLYTPASLK
           60         70         80         90        100
    CSLQNAQEAL IVTWQKKKAV SPENMVTFSE NHGVVIQPAY KDKINITQLG
          110        120        130        140        150
    LQNSTITFWN ITLEDEGCYM CLFNTFGFGK ISGTACLTVY VQPIVSLHYK
          160        170        180        190        200
    FSEDHLNITC SATARPAPMV FWKVPRSGIE NSTVTLSHPN GTTSVTSILH
          210        220        230        240        250
    IKDPKNQVGK EVICQVLHLG TVTDFKQTVN KGYWFSVPLL LSIVSLVILL
          260
    VLISILLYWK RHRNQDREP  (SEQ ID NO : 10)
```

C)

```
           10         20         30         40         50
    MERLTLTRTI GGPLLTATLL GKTTINDYQV IRMFFSHLST YSLVWVMAAV
           60         70         80         90        100
    VLCTAQVQVV TQDEREQLYT PASLKCSLQN AQEALIVTWQ KKKAVSPENM
          110        120        130        140        150
    VTFSENHGVV IQPAYKDKIN ITQLGLQNST ITFWNITLED EGCYMCLFNT
          160        170        180        190        200
    FGFGKISGTA CLTVYVQPIV SLHYKFSEDH LNITCSATAR PAPMVFWKVP
          210        220        230        240        250
    RSGIENSTVT LSHPNGTTSV TSILHIKDPK NQVGKEVICQ VLHLGTVTDF
          260        270        280        290
    KQTVNKGYWF SVPLLSIVS LVILLVLISI LLYWKRHRNQ DREP (SEQ ID NO : 11)
```

FIGURE 11 cont'd

D)
```
   1 gtcagtttcc ccagcggtca cctttgaaaa gggaaaaatg tctgaaaata gacaagctg
  61 aatataaaca tcatttaatt ccccccacac agacagcctc cgctcctgtg agggcgtggg
 121 gaaaacggag tgggagaagg gggctagcga ggaggaagag gcgggaggtg cgacagggc
 181 acaggtgacg ctcctcccgc ctgcctagca gagctccagg cgcacatccg cagtcagcca
 241 cctcgcgcgc gcctccagga gcaaggatgg agaggctggt gatcaggatg cccttctctc
 301 atctgtctac ctacagcctg gtttgggtca tggcagcagt ggtgctgtgc acagcacaag
 361 tgcaagtggt gacccaggat gaaagagagc agctgtacac acctgcttcc ttaaastgct
 421 ctctgcaaaa tgcccaggaa gccctcattg tgacatggca gaaaagaaa gctgtaagcc
 481 cagaaaacat ggtcaccttc agcgagaacc atgggtggt gatccagcct gcctataagg
 541 acaagataaa cattacccag ctgggactcc aaastcaac catcaccttc tggaatatca
 601 ccctggagga tgaagggtgt acatgtgtc tcttcaatac ctttggtttt gggaagatct
 661 caggaacggc ctgcctcacc gtctatgtac agcccatagt atcccttcac tacaaattct
 721 ctgaagacca cctaatatc acttgtctg ccactgcccg cccagcccc atggtcttct
 781 ggaaggtccc tcggtcaggg attgaaaata gtacagtgac tctgtctcac ccaaatggga
 841 ccagtctgt taccagcatc ctccatatca aagaccctaa gaatcagtg gggaaggagg
 901 tgatctgcca ggtgctgcac ctgggactg tgaccgactt taagcaaacc gtcaacaaag
 961 gctattggtt ttcagttccg ctattgctaa gcattgtttc cctggtaatt cttctcgtcc
1021 taatctcaat cttactgtac tggaaacgtc accggaatca ggaccgagag ccctaaataa
1081 gtcacacagc accctgaaag tgattccctg gtctacttga atttgacaca agagaaaagc
1141 aggaggaaaa ggggccattc tccaaaggac ctgaaagagc aaaagaggtg ggagcgaaag
1201 ccttaaggat cccacgactt tttactgcca tctgagctac tcagtgtttg aatccaaga
1261 ggaagtcagt ttacctctca ggtctgttgt aggacttgat tttgtaaagc aatgccatgt
1321 tatgtgttg aaagggcact ggacttagtt agtatcagga gcactgagct cacagactga
1381 cttggctcc tactggtggg gacctctgtt agtcacttta cctcatccaa agtataaagg
1441 aattggacca ataaatttac cacatagctc taaaacttaa tttaaaatgt aattccagaa
1501 aaaaaaggg aataagcaaa ggggaagaa ttaaagaga gagagaagaa agaatacaga
1561 gagcttacct tttgccttc tgttgatgtt acatctcctc ttcctatgtt cttaggtcta
1621 tgagtctgtt tccccatcat ttggtatcta gtccagttcc tgcttactgc tttgctaata
1681 gctgccttg ctagaatcct tggtttcact gctgttcttc atgtgcttct atgagatcta
1741 ctccaacaca aataggactg aatttatcgt gaagtaacat tggcaatctt aacttattca
1801 tttaacttat ttttatagct agataaatat tgttagtctt agacaatagc tcacattttt
1861 tgagaagcat gccctccctg tccatttgtc ttataacatg accagccct attttacgtc
1921 attctaaatt cagcctcata taatgaaaat acattatgaa aacagatgtt taggagattt
1981 cctgtatagc agtcagccaa ttcatatgct ttgtctctgc tggcttcttt ttccatgcgt
2041 taacttttcc caatagcaga ggagcaaat atgagcatac aatcccttg ttctaaagat
2101 attgttccag ctagtggaat gatgttgaat cttaataac cataattagt tgcttttca
2161 gtatcttctg ctttgtctgt gtctatccag tggcctagga attaaagtgt aagttgttt
2221 cgctgttaaa ttggatattt atatatatat atagcaagat tttcatgtgt tatttaattc
2281 tgtattgttt cttatatttg tagtaaaata ttgaacaatt aaaagtgttg actccaaaaa
2341 aaaaaaaa   (SEQ ID NO: 12
```

MLCPWRTANLGLLLILTIFLVAEAEGAAQPNNSLMLQTSKENHA
LASSSLCMDEKQITQNYSKVLAEVNTSWPVKMATNAVLCCPPIALRNLIIITWEIILR
GQPSCTKAYKKETNETKETNCTDERITWVSRFDQNSDLQIRTVAITHDGYYRCIMVTP
DGNFHRGYHLQVLVTPEVTLFQNRNRTAVCKAVAGKPAAHISWIPEGDCATKQEYWSN
GTVTVKSTCHWEVHNVSTVTCHVSHLTGNKSLYIELLPVPGAKKSAKLYIPYIILTII
ILTIVGFIWLLKVNGCRKYKLNKTESTPVVEEDEMQPYASYTEKNNPLYDTTNKVKAS
EALQSEVDTDLHTL  (SEQ ID NO: 13)

B)

```
  1 attgctgtgt caagttccag agaaaagctt ctgttcgtcc aagttactaa ccaggctaaa
 61 ccacatagac gtgaaggaag gggctagaag gaagggagtg cccactgtt gatggggtaa
121 gaggatcctg tactgagaag ttgaccagag agggtctcac catgcgcaca gttccttctg
181 tacctgtgtg gaggaaaagt actgagtgaa gggcagaaaa agagaaaaca gaaatgctct
241 gcccttggag aactgctaac ctagggctac tgttgatttt gactatcttc ttagtggccg
301 aagcggaggg tgctgctcaa ccaaacaact cattaatgct gcaaactagc aaggagaatc
361 atgctttagc ttcaagcagt ttatgtatgg atgaaaaaca gattacacag aactactcga
421 aagtactcgc agaagttaac acttcatggc ctgtaaagat ggctacaaat gctgtgcttt
481 gttgccctcc tatcgcatta agaaatttga tcataataac atgggaaata atcctgagag
541 gccagcctc ctgcacaaaa gctacaaga aagaaacaaa tgagaccaag gaaaccaact
601 gtactgatga gagaataacc tgggtctcca gacctgatca gaattcggac cttcagattc
661 gtaccgtggc catcactcat gacgggtatt acagatgcat aatggtaaca cctgatggga
721 atttccatcg tggatatcac ctccaagtgt tagttacacc tgaagtgacc ctgtttcaaa
781 acaggaatag aactgcagta tgcaaggcag ttgcagggaa gccagctgcg catatctcct
841 ggatcccaga gggcgattgt gccactaagc aagaatactg gagcaatggc acagtgactg
901 ttaagagtac atgccactgg gaggtccaca tgtgtctac cgtgacctgc cacgtctccc
```

FIGURE 12 cont'd

```
 961 atttgactgg caacaagagt ctgtacatag agctacttcc tgttccaggt gccaaaaat
1021 cagcaaaatt atatattcca tatatcatcc ttactattat tattttgacc atcgtggat
1081 tcatttggtt gttgaaagtc aatggctgca gaaaatataa attgaataaa acagaatcta
1141 ctccagttgt tgaggaggat gaaatgcagc cctatgccag ctacacagag aagaacaatc
1201 ctctctatga tactacaaac aaggtgaagg catctgaggc attacaaagt gaagttgaca
1261 cagacctcca tacttttataa gttgttggac tctagtacca agaaacaaca acaaacgaga
1321 tacattataa ttactgtctg attttcttac agttctagaa tgaagactta tattgaaatt
1381 aggttttcca aggttcttag aagacatttt aatggattct cattcatacc cttgtataat
1441 tggaatttt gattcttagc tgctaccagc tagttctctg aagaactgat gttattacaa
1501 agaaaataca tgcccatgac caaatattca aattgtcag gacagtaaat aatgaaaacc
1561 aaatttcctc aagaaataac tgaagaagga gcaagtgtga acagtttctt gtgtatcctt
1621 tcagaatatt ttaatgtaca tatgacatgt gtatatgcct atggtatatg tgtcaattta
1681 tgtgtccct tacatataca tgcacatatc tttgtcaagg caccagtggg aacaatacac
1741 tgcattactg ttctatacat atgaaaacct aataatataa gtcttagaga tcatttata
1801 tcatgacaag tagagctacc tcattctttt taatggttat ataaaattcc attgtatagt
1861 tatatcatta tttaattaaa acaaccctta atgatggata tttagattct tttaagtttt
1921 gtttatttct tttaagtttt gtttgtggta taaacaatac cacatagaat gtttcttgtg
1981 catatatctc tttgttttg agtatatctg taggataact ttcttgagtg gaattgtcag
2041 gtcaagggt ttgtgcattt tactattgat atatatgtta aattgtgtca aatatatatg
2101 tcaaattccc tccaacattg tttaaatgtg cctttcccta aatttctatt ttaataactg
2161 tactattcct gcttctacag ttgccacttt ctcttttaa tcaaccagat taaatatgat
2221 gtgagattat aataagaatt atactattta ataaaatgg atttatattt tt
```

(SEQ ID NO:14)

B)

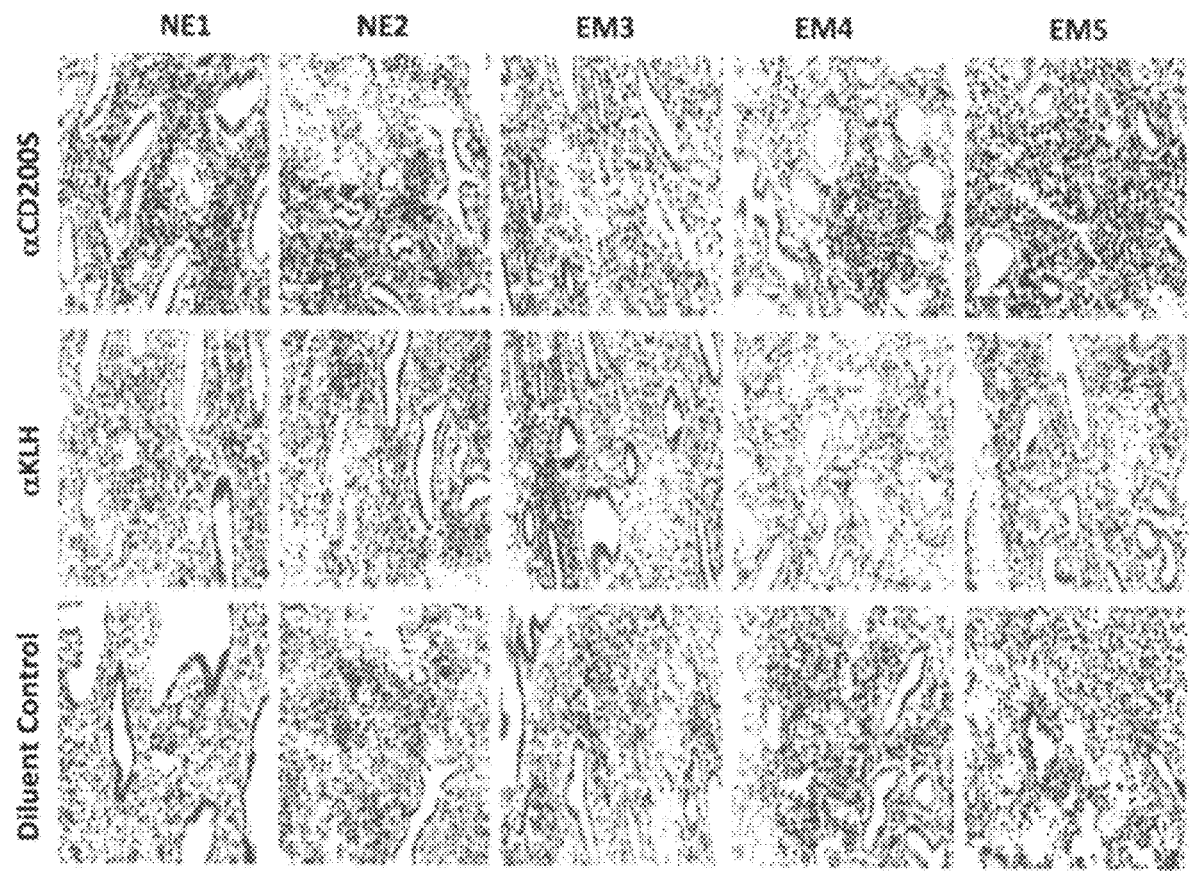

SEQUENCE LISTING

<160> NUMBER OF SEQ ID NOS: 14

<210> SEQ ID NO 1
<211> LENGTH: 20
<212> TYPE: DNA
<213> ORGANISM: Artificial
<220> FEATURE:
<223> OTHER INFORMATION: PCR primer

<400> SEQUENCE: 1
acccaggatg aaagagagca                                           20

<210> SEQ ID NO 2
<211> LENGTH: 20
<212> TYPE: DNA
<213> ORGANISM: Artificial
<220> FEATURE:
<223> OTHER INFORMATION: PCR primer

<400> SEQUENCE: 2
tataggcagg ctggatcacc                                           20

<210> SEQ ID NO 3
<211> LENGTH: 15
<212> TYPE: DNA
<213> ORGANISM: Artificial
<220> FEATURE:
<223> OTHER INFORMATION: PCR primer

<400> SEQUENCE: 3
ccatttgact ggcaa                                                15

<210> SEQ ID NO 4
<211> LENGTH: 20
<212> TYPE: DNA
<213> ORGANISM: Artificial
<220> FEATURE:
<223> OTHER INFORMATION: PCR primer

<400> SEQUENCE: 4
gcagccattg actttcaaca                                           20

<210> SEQ ID NO 5
<211> LENGTH: 20
<212> TYPE: DNA
<213> ORGANISM: Artificial
<220> FEATURE:
<223> OTHER INFORMATION: PCR primer

<400> SEQUENCE: 5
caaggcagtt acagggaagc                                           20

<210> SEQ ID NO 6
<211> LENGTH: 20
<212> TYPE: DNA
<213> ORGANISM: Artificial
<220> FEATURE:
<223> OTHER INFORMATION: PCR primer

<400> SEQUENCE: 6
gccagtcaaa tgggagacat                                           20

<210> SEQ ID NO 7
<211> LENGTH: 25
<212> TYPE: DNA
<213> ORGANISM: Artificial

```
<220> FEATURE:
<223> OTHER INFORMATION: PCR primer

<400> SEQUENCE: 7
tcaacgacca ctttgtcaaa cctca                                              25

<210> SEQ ID NO 8
<211> LENGTH: 23
<212> TYPE: DNA
<213> ORGANISM: Artificial
<220> FEATURE:
<223> OTHER INFORMATION: PCR primer

<400> SEQUENCE: 8
gctggtggtc cagggtctt act                                                 23

<210> SEQ ID NO 9
<211> LENGTH: 278
<212> TYPE: PRT
<213> ORGANISM: Homo sapiens

<400> SEQUENCE: 9
```

Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
            20                  25                  30

Gln Val Val Thr Gln Asp Glu Arg Glu Gln Leu Tyr Thr Pro Ala Ser
        35                  40                  45

Leu Lys Cys Ser Leu Gln Asn Ala Gln Glu Ala Leu Ile Val Thr Trp
50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95

Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Phe
        115                 120                 125

Gly Lys Ile Ser Gly Thr Ala Cys Leu Thr Val Tyr Val Gln Pro Ile
130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205

Gly Lys Glu Val Ile Cys Gln Val Leu His Leu Gly Thr Val Thr Asp
210                 215                 220

Phe Lys Gln Thr Val Asn Lys Gly Tyr Trp Phe Ser Val Pro Leu Leu
225                 230                 235                 240

Leu Ser Ile Val Ser Leu Val Ile Leu Leu Val Leu Ile Ser Ile Leu
                245                 250                 255

Leu Tyr Trp Lys Arg His Arg Asn Gln Asp Arg Gly Glu Leu Ser Gln
            260                 265                 270

Gly Val Gln Lys Met Thr

```
                        275

<210> SEQ ID NO 10
<211> LENGTH: 269
<212> TYPE: PRT
<213> ORGANISM: Homo sapiens

<400> SEQUENCE: 10

Met Glu Arg Leu Val Ile Arg Met Pro Phe Ser His Leu Ser Thr Tyr
1               5                   10                  15

Ser Leu Val Trp Val Met Ala Ala Val Leu Cys Thr Ala Gln Val
            20                  25                  30

Gln Val Val Thr Gln Asp Glu Arg Glu Gln Leu Tyr Thr Pro Ala Ser
        35                  40                  45

Leu Lys Cys Ser Leu Gln Asn Ala Gln Glu Ala Leu Ile Val Thr Trp
    50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95

Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Phe
        115                 120                 125

Gly Lys Ile Ser Gly Thr Ala Cys Leu Thr Val Tyr Val Gln Pro Ile
    130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205

Gly Lys Glu Val Ile Cys Gln Val Leu His Leu Gly Thr Val Thr Asp
    210                 215                 220

Phe Lys Gln Thr Val Asn Lys Gly Tyr Trp Phe Ser Val Pro Leu Leu
225                 230                 235                 240

Leu Ser Ile Val Ser Leu Val Ile Leu Leu Val Leu Ile Ser Ile Leu
                245                 250                 255

Leu Tyr Trp Lys Arg His Arg Asn Gln Asp Arg Glu Pro
            260                 265

<210> SEQ ID NO 11
<211> LENGTH: 294
<212> TYPE: PRT
<213> ORGANISM: Homo sapiens

<400> SEQUENCE: 11

Met Glu Arg Leu Thr Leu Thr Arg Thr Ile Gly Gly Pro Leu Leu Thr
1               5                   10                  15

Ala Thr Leu Leu Gly Lys Thr Thr Ile Asn Asp Tyr Gln Val Ile Arg
            20                  25                  30

Met Pro Phe Ser His Leu Ser Thr Tyr Ser Leu Val Trp Val Met Ala
        35                  40                  45

Ala Val Val Leu Cys Thr Ala Gln Val Gln Val Val Thr Gln Asp Glu
```

```
            50                  55                  60
Arg Glu Gln Leu Tyr Thr Pro Ala Ser Leu Lys Cys Ser Leu Gln Asn
 65                  70                  75                  80

Ala Gln Glu Ala Leu Ile Val Thr Trp Gln Lys Lys Ala Val Ser
                 85                  90                  95

Pro Glu Asn Met Val Thr Phe Ser Glu Asn His Gly Val Val Ile Gln
                100                 105                 110

Pro Ala Tyr Lys Asp Lys Ile Asn Ile Thr Gln Leu Gly Leu Gln Asn
            115                 120                 125

Ser Thr Ile Thr Phe Trp Asn Ile Thr Leu Glu Asp Glu Gly Cys Tyr
        130                 135                 140

Met Cys Leu Phe Asn Thr Phe Gly Phe Gly Lys Ile Ser Gly Thr Ala
145                 150                 155                 160

Cys Leu Thr Val Tyr Val Gln Pro Ile Val Ser Leu His Tyr Lys Phe
                165                 170                 175

Ser Glu Asp His Leu Asn Ile Thr Cys Ser Ala Thr Ala Arg Pro Ala
            180                 185                 190

Pro Met Val Phe Trp Lys Val Pro Arg Ser Gly Ile Glu Asn Ser Thr
        195                 200                 205

Val Thr Leu Ser His Pro Asn Gly Thr Thr Ser Val Thr Ser Ile Leu
    210                 215                 220

His Ile Lys Asp Pro Lys Asn Gln Val Gly Lys Glu Val Ile Cys Gln
225                 230                 235                 240

Val Leu His Leu Gly Thr Val Thr Asp Phe Lys Gln Thr Val Asn Lys
                245                 250                 255

Gly Tyr Trp Phe Ser Val Pro Leu Leu Leu Ser Ile Val Ser Leu Val
            260                 265                 270

Ile Leu Leu Val Leu Ile Ser Ile Leu Leu Tyr Trp Lys Arg His Arg
        275                 280                 285

Asn Gln Asp Arg Glu Pro
    290

<210> SEQ ID NO 12
<211> LENGTH: 2348
<212> TYPE: DNA
<213> ORGANISM: Homo sapiens

<400> SEQUENCE: 12
gtcagtttcc ccagcggtca cctttgaaaa gggaaaaatg tctgaaaata gacaaagctg      60
aatataaaca tcatttaatt ccccccacac agacagcctc cgctcctgtg agggcgtggg     120
gaaaacggag tgggagaagg gggctagcga ggaggaagag gcgggaggtg cggcaggggc     180
acaggtgacg ctcctcccgc ctgcctagca gagctccagg cgcacatccg cagtcagcca     240
cctcgcgcgc gcctccagga gcaaggatgg agaggctggt gatcaggatg cccttctctc     300
atctgtctac ctacagcctg gtttgggtca tggcagcagt ggtgctgtgc acagcacaag     360
tgcaagtggt gacccaggat gaaagagagc agctgtacac acctgcttcc ttaaaatgct     420
ctctgcaaaa tgcccaggaa gccctcattg tgacatggca gaaaaagaaa gctgtaagcc     480
cagaaaacat ggtcaccttc agcgagaacc atggggtgga tccagcct gcctataagg       540 acaagataaa cattacccag ctgggactcc aaaactcaac catcaccttc tggaatatca     600
ccctggagga tgaagggtgt tacatgtgtc tcttcaatac ctttggtttt gggaagatct     660
caggaacggc ctgcctcacc gtctatgtac agcccatagt atcccttcac tacaaattct     720
```

-continued

| | |
|---|---|
| ctgaagacca cctaaatatc acttgctctg ccactgcccg cccagccccc atggtcttct | 780 |
| ggaaggtccc tcggtcaggg attgaaaata gtacagtgac tctgtctcac ccaaatggga | 840 |
| ccacgtctgt taccagcatc ctccatatca aagaccctaa gaatcaggtg gggaaggagg | 900 |
| tgatctgcca ggtgctgcac ctggggactg tgaccgactt taagcaaacc gtcaacaaag | 960 |
| gctattggtt ttcagttccg ctattgctaa gcattgtttc cctggtaatt cttctcgtcc | 1020 |
| taatctcaat cttactgtac tggaaacgtc accggaatca ggaccgagag ccctaaataa | 1080 |
| gtcacacagc accctgaaag tgattccctg gtctacttga atttgacaca agagaaaagc | 1140 |
| aggaggaaaa ggggccattc tccaaaggac ctgaaagagc aaaagaggtg ggagcgaaag | 1200 |
| ccttaaggat cccacgactt tttactgcca tctgagctac tcagtgtttg aatcccaaga | 1260 |
| ggaagtcagt ttacctctca ggtctgttgt aggacttgat tttgtaaagc aatgccatgt | 1320 |
| tatgtggttg aaagggcact ggacttagtt agtatcagga gcactgagct cacagactga | 1380 |
| cttgggctcc tactggtggg gacctctgtt agtcacttta cctcatccaa agtataaagg | 1440 |
| aattggacca ataatttac cacatagctc taaaacttaa tttaaaatgt aattccagaa | 1500 |
| aaaaaaggg aataagcaaa gggggaagaa ttgaaagaga gagagaagaa agaatacaga | 1560 |
| gagcttacct tttgcctttc tgttgatgtt acatctcttc ttcctatgtt cttaggtcta | 1620 |
| tgagtctgtt tccccatcat ttggtatcta gtccagttcc tgcttactgc tttgctaata | 1680 |
| gctggccttg ctagaatcct tggtttcact gctgttcttc atgtgcttct atgagattta | 1740 |
| ctccaacaca aataggactg aatttattgt gaagtaacat ggcaatctt aacttattca | 1800 |
| tttaacttat ttttatagct agataaatat tgttagtctt agacaatagc tcacatttt | 1860 |
| tgagaagcat gccctccctg tccatttgtc ttataacatg acccagccct attttacgtc | 1920 |
| attctaaatt cagcctcata taatgaaaat acattatgaa aacagatgtt taggagattt | 1980 |
| cctgtatagc agtcagccaa ttcatatgct ttgtctctgc tggcttcttt ttccatgcgt | 2040 |
| taacttttcc caatagcaga ggaggcaaat atgagcatac aatccctttg ttctaaagat | 2100 |
| attgttccag ctagtggaat gatgttgaat ctttaataac cataattagt tgcttttttca | 2160 |
| gtatcttctg ctttgtctgt gtctatccag tggcctagga attaaagtgt aagttgtttt | 2220 |
| cgctgttaaa ttggatattt atatatatat atagcaagat tttcatgtgt tatttaattc | 2280 |
| tgtattgttt cttatatttg tagtaaaata ttgaacaatt aaaagtgttg actccaaaaa | 2340 |
| aaaaaaaa | 2348 |

<210> SEQ ID NO 13
<211> LENGTH: 348
<212> TYPE: PRT
<213> ORGANISM: Mus sp.

<400> SEQUENCE: 13

Met Leu Cys Pro Trp Arg Thr Ala Asn Leu Gly Leu Leu Leu Ile Leu
1               5                   10                  15

Thr Ile Phe Leu Val Ala Glu Ala Glu Gly Ala Ala Gln Pro Asn Asn
                20                  25                  30

Ser Leu Met Leu Gln Thr Ser Lys Glu Asn His Ala Leu Ala Ser Ser
            35                  40                  45

Ser Leu Cys Met Asp Glu Lys Gln Ile Thr Gln Asn Tyr Ser Lys Val
        50                  55                  60

Leu Ala Glu Val Asn Thr Ser Trp Pro Val Lys Met Ala Thr Asn Ala
65                  70                  75                  80

Val Leu Cys Cys Pro Ile Ala Leu Arg Asn Leu Ile Ile Ile Thr
            85                  90                  95

Trp Glu Ile Ile Leu Arg Gly Gln Pro Ser Cys Thr Lys Ala Tyr Lys
        100                 105                 110

Lys Glu Thr Asn Glu Thr Lys Glu Thr Asn Cys Thr Asp Glu Arg Ile
            115                 120                 125

Thr Trp Val Ser Arg Pro Asp Gln Asn Ser Asp Leu Gln Ile Arg Thr
130                 135                 140

Val Ala Ile Thr His Asp Gly Tyr Tyr Arg Cys Ile Met Val Thr Pro
145                 150                 155                 160

Asp Gly Asn Phe His Arg Gly Tyr His Leu Gln Val Leu Val Thr Pro
                165                 170                 175

Glu Val Thr Leu Phe Gln Asn Arg Asn Arg Thr Ala Val Cys Lys Ala
            180                 185                 190

Val Ala Gly Lys Pro Ala Ala His Ile Ser Trp Ile Pro Glu Gly Asp
        195                 200                 205

Cys Ala Thr Lys Gln Glu Tyr Trp Ser Asn Gly Thr Val Thr Val Lys
    210                 215                 220

Ser Thr Cys His Trp Glu Val His Asn Val Ser Thr Val Thr Cys His
225                 230                 235                 240

Val Ser His Leu Thr Gly Asn Lys Ser Leu Tyr Ile Glu Leu Leu Pro
                245                 250                 255

Val Pro Gly Ala Lys Lys Ser Ala Lys Leu Tyr Ile Pro Tyr Ile Ile
            260                 265                 270

Leu Thr Ile Ile Ile Leu Thr Ile Val Gly Phe Ile Trp Leu Leu Lys
        275                 280                 285

Val Asn Gly Cys Arg Lys Tyr Lys Leu Asn Lys Thr Glu Ser Thr Pro
    290                 295                 300

Val Val Glu Glu Asp Glu Met Gln Pro Tyr Ala Ser Tyr Thr Glu Lys
305                 310                 315                 320

Asn Asn Pro Leu Tyr Asp Thr Thr Asn Lys Val Lys Ala Ser Glu Ala
                325                 330                 335

Leu Gln Ser Glu Val Asp Thr Asp Leu His Thr Leu
            340                 345

<210> SEQ ID NO 14
<211> LENGTH: 2272
<212> TYPE: DNA
<213> ORGANISM: Mus sp.

<400> SEQUENCE: 14
attgctgtgt caagttccag agaaaagctt ctgttcgtcc aagttactaa ccaggctaaa     60
ccacatagac gtgaaggaag gggctagaag gaagggagtg ccccactgtt gatggggtaa    120
gaggatcctg tactgagaag ttgaccagag agggtctcac catgcgcaca gttccttctg    180
tacctgtgtg gaggaaaagt actgagtgaa gggcagaaaa agagaaaaca gaaatgctct    240
gcccttggag aactgctaac ctagggctac tgttgatttt gactatcttc ttagtggccg    300
aagcggaggg tgctgctcaa ccaaacaact cattaatgct gcaaactagc aaggagaatc    360
atgctttagc ttcaagcagt ttatgtatgg atgaaaaaca gattacacag aactactcga    420
aagtactcgc agaagttaac acttcatggc ctgtaaagat ggctacaaat gctgtgcttt    480
gttgccctcc tatcgcatta agaaatttga tcataataac atgggaaata atcctgagag    540
gccagccttc ctgcacaaaa gcctacaaga agaaacaaa tgagaccaag gaaccaact    600

```
                                                         -continued
gtactgatga gagaataacc tgggtctcca gacctgatca gaattcggac cttcagattc    660
gtaccgtggc catcactcat gacgggtatt acagatgcat aatggtaaca cctgatggga    720
atttccatcg tggatatcac ctccaagtgt tagttacacc tgaagtgacc ctgtttcaaa    780
acaggaatag aactgcagta tgcaggcag ttgcagggaa gccagctgcg catatctcct     840
ggatcccaga gggcgattgt gccactaagc aagaatactg gagcaatggc acagtgactg    900
ttaagagtac atgccactgg gaggtccaca atgtgtctac cgtgacctgc cacgtctccc    960
atttgactgg caacaagagt ctgtacatag agctacttcc tgttccaggt gccaaaaaat   1020
cagcaaaatt atatattcca tatatcatcc ttactattat tattttgacc atcgtgggat   1080
tcatttggtt gttgaaagtc aatggctgca gaaaatataa attgaataaa acagaatcta   1140
ctccagttgt tgaggaggat gaaatgcagc cctatgccag ctacacagag aagaacaatc   1200
ctctctatga tactacaaac aaggtgaagg catctgaggc attacaaagt gaagttgaca   1260
cagacctcca tactttataa gttgttggac tctagtacca agaaacaaca acaaacgaga   1320
tacattataa ttactgtctg attttcttac agttctagaa tgaagactta tattgaaatt   1380
aggttttcca aggttcttag aagacatttt aatggattct cattcatacc cttgtataat   1440 tggaatttt gattcttagc tgctaccagc tagttctctg aagaactgat gttattacaa    1500
agaaaataca tgcccatgac caaatattca aattgtgcag gacagtaaat aatgaaaacc   1560
aaatttcctc aagaaataac tgaagaagga gcaagtgtga acagtttctt gtgtatcctt   1620
tcagaatatt ttaatgtaca tatgacatgt gtatatgcct atggtatatg tgtcaattta   1680
tgtgtcccct tacatataca tgcacatatc tttgtcaagg caccagtggg aacaatacac   1740
tgcattactg ttctatacat atgaaaacct aataatataa gtcttagaga tcattttata   1800
tcatgacaag tagagctacc tcattctttt taatggttat ataaaattcc attgtatagt   1860
tatatcatta tttaattaaa aacaaccta atgatggata tttagattct tttaagtttt    1920
gtttatttct tttaagtttt gtttgtggta taaacaatac cacatagaat gtttcttgtg   1980
catatatctc tttgtttttg agtatatctg taggataact ttcttgagtg gaattgtcag   2040
gtcaaagggt ttgtgcattt tactattgat atatatgtta aattgtgtca aatatatatg   2100
tcaaattccc tccaacattg tttaaatgtg cctttcccta aatttctatt ttaataactg   2160
tactattcct gcttctacag ttgccacttt ctcttttttaa tcaaccagat taaatatgat  2220
gtgagattat aataagaatt atactattta ataaaaatgg atttatattt tt           2272
```

METHODS FOR THE DIAGNOSIS AND TREATMENT OF ENDOMETRIOSIS

FIELD OF INVENTION

The present invention provides compositions and methods for the diagnosis, assessment, characterization and treatment of endometriosis in a subject in need thereof, based upon the expression level of a biomarker that is associated with endometriosis.

BACKGROUND OF THE INVENTION

Although menstrual tissue with blood is expelled primarily per vaginum, in 70-90% of women, some menstrual tissue refluxes back through the fallopian tubes into the peritoneal cavity and is thought to give rise to endometriosis, a concept originally proposed by Sampson (Clement, 2007; Bokor et al., 2009; Li et al., 2014). Endometrial epithelium and stroma successfully implants on the peritoneal surface of the uterus, ovary, pouch of Douglas peritoneum and other peritoneal surfaces such as the omentum (Clement, 2007; Bokor et al., 2009; Li et al., 2014). Successfully implanted peritoneal deposits of endometrial cells stimulated by estrogen can grow, cause local inflammation with release of Th1 cytokines that inhibit sperm-oocyte interactions (even in infertile patients where endometriotic implants are not visible), and eventually, may lead to fibrosis as the inflammatory/healing process burns out (Clement, 2007; Kalu et al., 2007). Although this process is reminiscent of surface spread of malignant tumor cells, endometriotic deposits are not usually invasive and are not usually found in lymph nodes. Endometriotic deposits have been occasionally seen in veins and skin, deposits in the liver and lung are extremely rare absent malignant transformation (Clement, 2007: Bokor et al., 2009; Yu et al., 2013; Liu et al., 2015). However, endometriotic deposits can develop in abdominal scars, and along needle biopsy tracks, supporting the idea that the ability of endometrial cells to establish extrauterine deposits is an inherent property of the endometrial cells (Wolf and Singh, 1989). Ridley and Edwards have reported successful autologous menstrual blood cell implantation in the suprapubic area adjacent to peritoneal fascia with ⅛ women developing an endometrioma and ⅔ having a foreign body/scarring reaction (Ridley and Edwards, 1958). Human endometrium as well as endometriosis tissue has been successfully xenotransplanted into immunodeficient nu/nu mice with >80% success and no evidence that proliferative and secretory phase endometrium were different in their ability to implant (Zamah et al., 1984). A similar result was obtained with autologous endometrium in monkeys and also using menstrually shed endometrial cells but the success rate in establishing endometriosis was less than in the xenotransplant mouse model (Zamah et al., 1984; Te Linde and Scott, 1950; Scott and Te Linde, 1954).

The implantation efficiency of endometrial cells entering into the peritoneal cavity at the time of menstruation is estimated to be only 11-14% in the 90% of women with retrograde menstruation (Clement, 2007; Bokor et al., 2009; Li et al., 2014). Many factors have been suggested to play a role in the implantation efficiency. In a mouse model, a larger dose of endometrial cells plus administration of estrogen has been shown to be critical (Somigliana et al., 1999). Estrogen is also permissive for human endometriosis (Tirado-Gonzalez et al., 2010; Xu et al., 2013; Mei et al., 2015). Gargett et al., (2014) have postulated that reflux of endometrial stem cells into the peritoneal cavity occurs in 5% of female neonates, and later in life (albeit sometimes before adolescence) and these stem cells become activated and cause early onset endometriosis. In adult women, higher frequencies of endometrial stem cells in menstrual blood and peritoneal fluid may similarly predispose to endometriosis (Gargette et al., 2014).

Notwithstanding the inherent autotransplantability and dose of endometrial cells delivered to the peritoneal cavity (the seed), there appears to be critically important co-factors required to ensure the peritoneal environment (the soil) is hospitable. For example, NK cell suppression facilitates grafting, whereas cytokines such as IL-2 and IL-12 that activate NK cells have been shown to be inhibitory (Somigliana et al., 1999). In endometriosis, there is suppression of innate effector cells such as cytolytic $CD56^+$ $CD16^+$ NK cells (Vigano et al., 1991; Jones et al., 1996; Berbic and Fraser, 2011) and based on animal model data, suppression of NK cells appears important for establishment of ectopic implants (Somigliana et al., 1999). Upregulation of IDO in endometrial stromal cells promotes growth and augments production of IL-33 which renders macrophages 'tolerant' (Mei et al., 2012, 2013). IDO also degrades tryptophan into molecules that enhance the generation of regulatory T cells (Tregs), that suppress rejection, suppress NK cells, and render macrophages 'tolerant' (Clark, 2016a). Treg suppressor activity similar to what is required for normal embryo implantation in pregnancy occurs in endometriotic deposits and originating endometrium, along with production of IDO that promotes Tregs, and recruitment of 'tolerant' myeloid-derived suppressor macrophage-type cells (Berbic et al., 2010; Berbic and Fraser, 2011; Clark, 2016a). The macrophages in ectopic implants produce growth factors as well as IDO which stimulates macrophages to produce the immunosuppressive cytokine IL-10 and fibrogenic cytokine TGF-β, and also stimulates endometriotic cell growth and invasion (Mei et al., 2012, 2015).

Treg cells are present in ectopic and eutopic endometrium of endometriosis patients and are proposed to play a key role in the establishment and progression of ectopic implants (Basta et al., 2010; Berbic et al., 2010; Berbic and Fraser, 2011). The role of Tregs cells is supported by studies of experimental endometriosis in mice, and may act in a number of ways (Budiu et al., 2009; Clark and Gorczynski, 2013; Woidacki et al., 2015). Tregs may also stimulate, directly or indirectly, angiogenic $CD56^{bright}CD16^-$ NK cells that home to inflammatory sites where they promote angiogenesis (albeit only 5% of leukocytes in endometriosis tissue are $CD56^+CD16^+$), angiogenic IDO-producing macrophages, angiogenic neutrophils and angiogenic mast cells (Dalbeh et al., 2004; Berbic and Fraser, 2011; Jetten et al., 2014; Clark, 2016a). Thus, a variety of processes dominated by Treg cells make the "soil" (i.e. peritoneum) favorable for refluxed shed endometrium to implant and grow.

One property of eutopic endometrium proposed to make it more likely to implant and grow when refluxed into the peritoneal cavity at the time of menstruation is reduced expression of IL-18. IL-18 normally promotes the cytolytic interferon-γ-producing type of cytolytic NK cells (Luo et al., 2006). IL-18 is another pro-inflammatory cytokine which may be suppressed in eutopic endometriosis along with other Th1 cytokines by Treg cells.

The CD200 tolerance signaling molecule is a glycoprotein that acts by binding to CD200 receptors which possess an intracellular signaling tail. Binding on dendritic cells promotes IDO production and promotes Treg generation, Binding to macrophages promotes IDO-production that enhances Treg generation and converts proinflammatory M1-type macrophages to 'tolerogenic' type M2 macrophages (Clark, 2016a). Tregs, as well as CD200 acting directly on CD200R, can suppress cytolytic NK cells that can reject deposition and survival of damaged/sloughed tissue (Clark and Gorczynski, 2013; Clark, 2016a, 2016b). CD200 can also directly suppress mast cells. Tregs are present in endometriosis deposits. It has been suggested by Berbic et al., (2010) and Berbic and Fraser (2011) that Treg cell levels may be higher in the pre-menstrual (secretory phase) endometrium of women who have endometriosis, although their identification of Tregs relied solely on expression of intracellular foxp3 which alone is now thought to be insufficient to identify Tregs in humans. CD200 is present in the trophoblast of early human embryos and plays an important role in ensuring pregnancy success by activating Tregs and suppressing harmful inflammation and NK cell cytotoxicity. CD200 is released in a bioactive soluble form (sCD200) and can act at a distance from the cell producing it (Wong et al., 2016).

However, eutopic endometrial parameters sufficient to predict endometriosis have not been identified to date. Berbic et al. (2010) reported more Foxp3$^+$ cells in the secretory phase endometrium of endometriosis patients, but with 21 controls and 25 patients, the standard deviation was so large as to indicate significant overlap, and only ⅓ of endometriosis patients had counts exceeding the 95% confidence range of normal non-endometriosis control patients. Thus, Foxp3 cell density in an individual would be predictive for only ⅓ of endometriosis patients. It should be noted that in humans, Foxp3 is expressed by activated T cells as well as by Treg cells, so Treg cell identification requires additional markers (Allan el al., 2007). With respect to IL-18, the levels in eutopic endometrium in endometriosis patients significantly overlap the normal control range (Luo et al., 2006), so the predictive value of IL-18 for endometriosis is no better than Foxp3. It has been mentioned that high IDO levels in endometrial stromal cells that induces production of IL-33 that promotes inflammation by binding to T1/ST2 receptors. Peritoneal IL-33 levels in early stage endometriosis are not different from the levels in non-endometriosis controls (Mbarik et al., 2015). IDO levels have only been quantified in endometriosis tissue and not in normal control tissue. Activated NK cells are implicated in preventing endometriosis, however, endometriosis can occur in spite of increased peritoneal NK activity (Somigliana et al., 1999; Wu et al., 2000). The susceptibility to suppression of NK cells in different individual may also vary (Somigliana et al., 2001).

This raises the question of genetic factors that might determine risk of endometriosis (Vigano et al., 2007). Genetic factors contribute increased risk of endometriosis based on twin studies (Treloar et al., 1999), but relevance for CD200 and CD200R expression is unknown. Gene expression in endometriomas differs from eutopic endometrium, which is explainable by inflammation at ectopic sites (Matsuzaki et al., 2006), and is complicated by the fact that peritoneal inflammation in endometriosis patients alters gene expression in eutopic endometrium (Brosens et al., 2012). None of the differences between eutopic endometrium in normal patients versus endometriosis patients can be considered a reliable indicator of what properties of eutopic endometrium predicted likelihood of developing endometriosis (Brosens et al., 2012).

Accordingly, it would be desirable to develop a novel method of diagnosing and treating endometriosis.

SUMMARY OF THE INVENTION

The present invention describes the finding that increased levels of CD200L are associated with endometriosis. CD200L is therefore a useful biomarker for the diagnosis of endometriosis and a useful target for therapeutic intervention.

In one aspect of the invention, a method of detecting CD200L in a secretory phase endometrial biological sample from a female mammal or subject is provided. The method comprises: i) obtaining the secretory phase biological sample from the subject, and ii) detecting whether or not CD200L is present in the biological sample by contacting the sample with an anti-CD200L antibody and detecting binding between CD200L and the antibody.

In another aspect, a method of diagnosing endometriosis in a subject is provided. The method comprises: a. obtaining a secretory phase endometrial biological sample from the subject, b. determining the level of CD200L, in the biological sample, c. comparing the level of CD200L in the biological sample with the level of CD200L in a comparator, wherein when the level of CD200L in the biological sample is higher than the level of CD200L in the comparator, the subject is diagnosed with endometriosis. In an embodiment, the method includes the step of treating the subject.

In another aspect, a method of monitoring a mammal following treatment of endometriosis is provided. The method comprises: determining the level of CD200L in a biological sample from the mammal and comparing the CD200L level to a control pre-treatment CD200L control level to determine if the CD200L level is reduced compared to the control level; and determining that the mammal is responding to treatment when the CD200L level is reduced in comparison to the control level.

In another aspect, a method of screening for a therapeutic agent useful for treating endometriosis is provided. The method comprises: contacting CD200L, a CD200R or both CD200L and a CD200R with the target agent; and detecting whether or not the agent binds CD200L or the CD200R, or otherwise modulates the function or expression of CD200L or the CD200R, wherein detection of binding to, or modulation of the function or expression of, CD200L or CD200R indicates that the agent is a potential therapeutic agent that may be useful to treat endometriosis.

In another aspect, a method of treating endometriosis is provided. The method comprises; administering a therapeutically effective amount of a compound that inhibits CD200L or a CD200R to a subject in need of treatment.

In a further aspect of the invention, a kit is provided comprising a CD200L-specific reactant for use in a method to detect the amount of CD200L in a secretory phase endometrial biological sample.

These and other aspects will become apparent by reference to the following Figures.

BRIEF DESCRIPTION OF THE DRAWINGS

Embodiments of the invention are described in more depth by reference to the following figures.

FIG. 11 illustrates the amino acid sequences of isoforms of cD200L (A/B/C) and the mRNA sequence of transcript 1 for CD200L (D).

FIG. 12 illustrates the amino acid (A) and mRNA (B) sequence of CD200R1.

DETAILED DESCRIPTION

Figure 1:
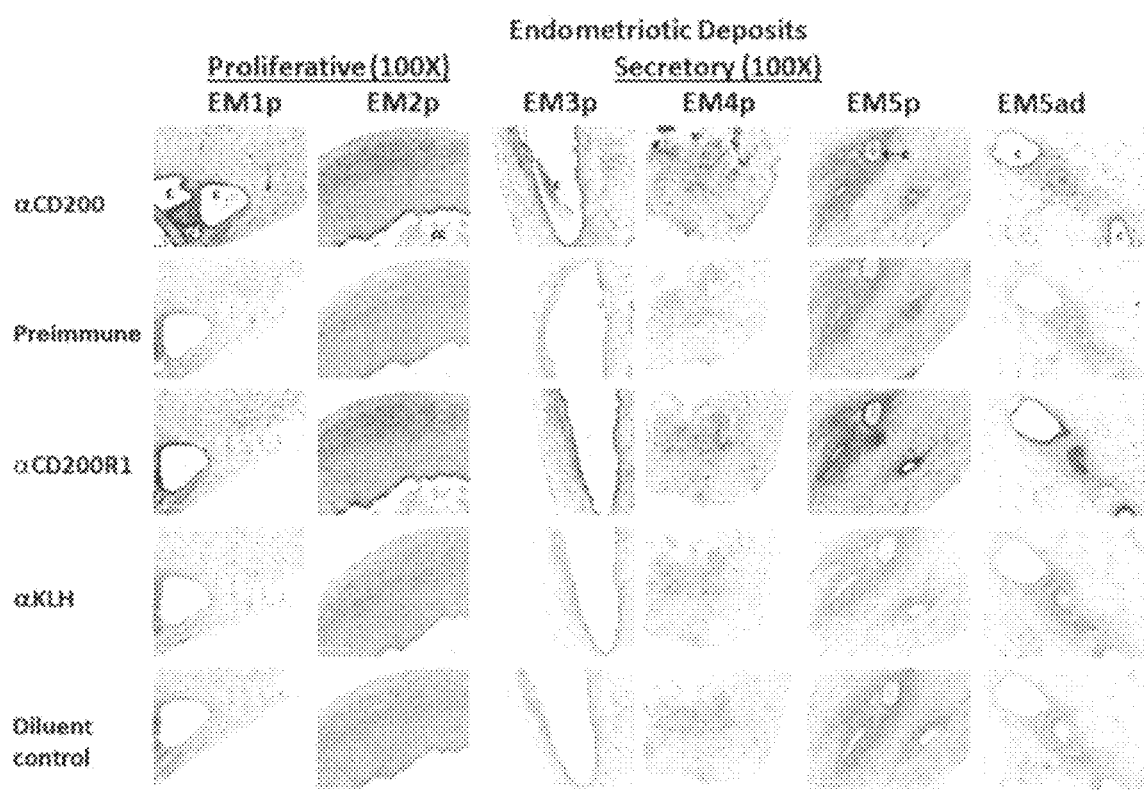
FIG. 1 is a depiction of the Endometriotic Deposits of 5 patients stained for CD200 and CD200R (dark staining). Samples EM1p and EM2p were peritoneal deposits (p) from patients in the proliferative phase of their menstrual cycle, and EM3p, EM4p, and EM5p were in the secretory phase of their cycle. EM5ad shows an endometriotic deposit in this patient's myometrium, called adenomyosis (ad). (100× magnification). c=cystic area, cc+chocolate cyst

A method of detecting CD200L in a secretory phase biological sample from a female mammal or subject is provided. The method comprises: i) obtaining the secretory phase biological sample from the subject, and ii) detecting whether or not CD200L is present in the biological sample by contacting the sample with an anti-CD200L antibody and detecting binding between CD200L and the antibody.

The female mammal may be a human or non-human mammal, and may be pre-symptomatic for endometriosis or may be displaying clinical symptoms suggestive of endometriosis.

CD200 or Cluster of Differentiation 200, also referred to as OX-2 membrane glycoprotein, is a type-1 membrane glycoprotein, contains two immunoglobulin domains, and thus belongs to the immunoglobulin superfamily. The term "CD200L" as used herein is meant to encompass mammalian CD200L, i.e. the wild-type non-truncated version incorporating exon 2, including functional equivalents thereof, such as isoforms, variants and orthologs. The canonical amino acid sequence of CD200L, isoform 1, is UniProt P41217-1 (see FIG. 11A) having 278 AA and an intracellular tail (amino acids 268-278). Isoform 2 (P41217-2) has 268-279 AA depending on whether the intracellular tail is as above or is just EP. Isoform 3 (P41217-3) has 269 AA, includes a 25 amino acid leader sequence, and EP as the intracellular tail. Variants include those in which one or more amino acids are altered without effect on function, e.g. amino acid at position 11 is C instead of S; amino acid at position 46 if T instead of P; and amino acid at position 76 is G instead of V. An example of a functionally equivalent ortholog includes a mouse protein encoded by a transcript such as NM_010818 (NCBI).

The present method includes the step of obtaining a secretory or menstrual phase endometrial biological sample. A secretory or menstrual phase biological sample includes a sample originating from the endometrium of the subject during the secretory and/or menstrual phase of the uterus. The sample may include peripheral blood, serum or plasma, urine, menstrual blood and/or discharge, uterine fluid, peritoneal fluid, an endometrial tissue sample (biopsy), and lymphatic or vascular fluid from secretory phase endometrium. The sample may be obtained using methods known in the art. Preferred samples include those obtained by non-invasive methods, such as shed endometrial fragments with blood present in menstrual discharge, preferably collected using a menstrual cup but also extractable from tampons. The amount of sample required will vary with the technique used to detect CD200L within the sample. Using an immunoassay such as an enzyme-linked immunoassay, an amount in the range of 0.1-0.3 ml of cell-free fluid may be sufficient. For tissue biopsy samples, generally 3-5 slides may be required.

Once the sample is obtained, it is then determined whether or not full-length CD200 (CD200L) is present in the sample. The presence of CD200L in the sample may be determined using a method that can distinguish between CD200L and the truncated form of CD200 (CD200tr or CD200S), a form resulting from a transcript missing exon 2, and thus, detect only CD200L.

In one embodiment, an immunoassay may be utilized to detect CD200L in the biological sample in which the sample is contacted with an anti-CD200L antibody to permit detection of CD200L. Suitable antibodies include those that detect the full-length CD200L and do not detect the truncated version (CD200tr or CD200S), i.e. antibodies that target an antigen within an amino acid region of CD200L encoded by exon 2 (e.g. an antibody raised against amino acids 45-95 of CD200L). Examples of suitable antibodies include, but are not limited to, a polyclonal antibody from Bioss (catalogue #bs-6030R). It may be advantageous to determine in a sample the percentage of CD200L and of CD200S. This is achieved by detecting CD200L as above using an antibody raised against amino acids encoded by exon 2, and detecting CD200L+CD200S using an antibody raised against amino acids encoded by exon 3 (i.e. amino acids 170-220, in the part of exon 3 not lost by the truncation of CD200L to form CD200S, namely a region beginning at amino acid position 124) such as a polyclonal antibody from Bioss (ABIN3187966). The results may be validated by Western blots of cell lysates that contain mRNA for CD200L and CD200S, using the primer sequences such as those published by Kobayashi et al. 2016).

Suitable immunoassays that may be employed to detect CD200L include, but are not limited to, enzyme-linked immunosorbent assays (ELISAs) or enzyme immunoassays (EIAs) in which an enzyme such as horseradish peroxidase (HRP), alkaline phosphatase (AP) or glucose oxidase permits detection of CD200L by emitting a detectable change (e.g. light, colour of chemiluminescence) in the presence of a certain reagent. A radioimmunoassay (RIA) may also be used to detect CD200L in which radioactive isotopes (e.g. $^{32}P$, $^{125}I$, $^{14}C$ and $^{3}H$) bound to the antibody-antigen complex emits radioactivity that may be detected. Immunoassays which use fluorogenic reporters such as phycoerythrin, fluorescein, rhodamine or cyanine dye, or which use electrochemiluminescent labels, such as ruthenium or terbium labels, may be used to detect CD200L.

Polymerase chain reaction (PCR) may also be used to detect CD200L in a biological sample utilizing nucleotide primer pairs that target exon 2 of CD200L DNA. In a preferred embodiment, Real-Time PCR or quantitative PCR (qPCR) may be used in which nucleic acid amplification and detection is conducted in a single step utilizing fluorescent labelled probes that hybridize to the target CD200L sequence and fluoresce when displaced during primer extension. As will be appreciated by one of skill in the art, suitable primer sets and probes for use in the present method are designed to hybridize to exon 2 of CD200L. Primer sequences are generally about 15 to 40 nucleotides in length, preferably 18-30 nucleotides in length, and are complementary to the terminal ends of a target exon 2 sequence. A probe, on the other hand, may be larger (e.g. 100 or more nucleotides) and is designed to hybridize to a region that is between the primer regions. As one of skill in the art will appreciate, primers and probes specific for exon 2 of CD200L may be designed based on the known sequence of CD200L. Software may be used which has been developed for this purpose. Examples of primers include those which target exon 2 (e.g. nucleotides nucleotides 361 . . . 687 of CD200L-encoding nucleic acid). The primers may span exons 2 and 3 and begin in exon 2 at a site that encodes amino acid at position 36 of the CD200L.

Detection of the level or concentration of CD200L in a secretory phase endometrial biological sample is useful in a method of diagnosing endometriosis in a subject. The level of CD200L in the biological sample is compared with the level of CD200L in a comparator, e.g. a control level of CD200L which reflects the level of CD200L in a corresponding secretory phase endometrial biological sample from a healthy female subject or population, i.e. females that do not have endometriosis. The comparator may also be a wild-type control level, a historical control level and a historical norm. Detection of a level of CD200L in the biological sample that is higher than the level of CD200L of the comparator non-endometriosis patients that show that no numerical overlap, e.g. such as 1 or 2 times higher, about 5 times higher or more, such as 8-10 times higher, 15 times higher, 20 times higher or more, indicates that subject is at risk of or has endometriosis. The level of CD200L may also be compared to CD200S in the sample as described above. When the ratio of CD200L/CD200S is high (e.g. level CD200L is greater than CD200S, evidenced by an increase in endometrial deposits since CD200L appears to be associated with endometrial deposits), this is indicative of endometriosis or risk of in a subject. A ratio of CD200L/CD200S that is decreased (e.g. level of CD200S is greater than CD200L, evidenced by rejection of endometrial deposits when tissue enters the peritoneal cavity at the time of menstruation) there is a reduced risk of endometriosis. Thus, CD200L is believed to possess immunosuppressive properties that permit engraftment of endometrial cells on peritoneal surface, while CD200S is believed to antagonize the immunosuppressive properties of CD200L.

The present method may also include the step of treating a subject determined to have endometriosis. Suitable treatments include administration of pain medication including NSAIDs (nonsteroidal anti-inflammatory drugs) such as ibuprofen or naproxen, or opioids such as codeine, fentanyl or methadone; hormone treatment that slows endometrial tissue growth and prevent new implants of endometrial tissue including administration of contraceptives including estrogen and progestin, or progestin alone; administration of gonadotropin-releasing hormone (GnRH) agonists such as buserelin, histrelin, leuprorelin, triptorelin, elagolix, letrozole or goserelin. These treatments are administered in a therapeutically effective amount, i.e. an amount suitable to treat or reduce the symptoms associated with endometriosis while not causing unacceptable adverse effects.

In another embodiment, endometriosis may be treated by administration of a therapeutically effective amount of a compound that inhibits the interaction of CD200L with its receptor, a CD200 receptor (CD200R such as CD200R1). The compound is not particularly restricted and may be a peptide, protein, peptidomimetic, antibody or antigenic fragment thereof that targets either CD200L or CD200R1, CD200L or CD200R1 binding fragment, soluble CD200R polypeptide, nucleotide such as an anti-sense nucleic acid or siRNA that targets either CD200L or CD200R1-encoding nucleic acid, or a small molecule inhibitory compound.

Examples of suitable inhibitors include antibodies such as, but not limited to, samalizumab, rituximab, ofatumumab, TRU-015, veltuzumab, ocrelizumab, or AME-133v. Other inhibitors of the CD200L/CD200R interaction include peptide inhibitors such as peptides derived from CD200L and CD200R1, including peptides from the N-terminal region of these proteins, for example, V-domain peptides from the CDR2 and CDR3 regions (e.g. a CD200L peptide comprising amino acids 62-75 and a peptide comprising amino acids 132-147), as well as 5-20 amino acid peptides as described in WO2017079335 and peptidomimetics derived there from. DNA-based inhibitors may also used, including antisense and siRNA molecules which are based on the mRNA or gene sequence of CD200, that bind to CD200 and prevent the CD200L/CD200R interaction. DNA aptamers that selectively recognize CD200R1 such as those described in U.S. Ser. No. 99/385,330 may also be used. Other CD200 inhibitors have been described by Kretz-Rommel (Journal of Immunology, 2008, 699-705); Chen (International Immunology, 17(3), 289-296 (2005)); Gorczynski (International Scholarly Research Network, ISRN Immunology, Volume 2012, Article ID 682168; pages 1-18); and in US Patent Publication No. 2002/0168364; U.S. Pat. No. 6,955,811; or U.S. Pat. No. 7,902,151, that may be used. The relevant portions of these references are incorporated herein by reference.

To complement this therapeutic approach, or as a stand-alone approach, CD200S may also be targeted to inhibit the initial inflammatory response required for implantation of ectopic tissue. As one of skill in the art will appreciate, the compound is not particularly restricted and may be a peptide, protein, peptidomimetic, antibody or antigenic fragment thereof, or small molecule inhibitory compound, that targets either CD200S or its receptor, or a nucleotide such as an anti-sense nucleic acid or siRNA that targets either the CD200S gene, or nucleic acid encoding its receptor.

In another aspect of the invention, a method to identify a target therapeutic agent useful for treating endometriosis is provided. The method comprises the steps of: contacting CD200L, a CD200R (such as CD200R1) or both CD200L and a CD200R with the target agent; and detecting whether or not the agent binds CD200L or the CD200R, wherein if the agent binds CD200L or CD200R, then the agent is a potential therapeutic agent that may be useful to treat endometriosis. The method may include the additional step of identifying whether or not the agent inhibits the interaction between CD200L and a CD200R to further confirm its potential use as a treatment for endometriosis.

In another aspect of the present invention, a method of monitoring a female mammal following treatment of endometriosis is provided. The method comprises: detecting the level of CD200L in a secretory phase endometrial biological sample from the mammal; comparing the detected CD200L level to a healthy control level or to a pre-treatment CD200L level in the mammal; and identifying that the mammal is responding to treatment when the CD200L level is reduced in comparison to the pre-treatment CD200L level, and/or is approaching the CD200L of the healthy control level.

In yet another aspect, a method of identifying risk of infertility in a female mammal is provided. The method comprises detecting the level of CD200R1 and CD200R2 in a biological sample from the mammal, comparing the level of CD200R1 to CD200R2 in the biological sample, and identifying that the mammal is at risk of infertility when the level of CD200R2 is higher than the level of CD200R1 in the biological sample. The biological sample may be a proliferative, secretory or menstrual phase sample. Preferably, the sample is a secretory phase sample.

In a further aspect of the invention, a kit is provided comprising a CD200L-specific reactant for use in a method to detect the amount of CD200L in a secretory phase endometrial biological sample. Examples of CD200L-specific reactants include antibodies that target exon 2 of CD200L as exemplified above. The kit may additionally include materials required to obtain a suitable sample such as means to collect menstrual blood. The kit may also optionally include instructions for use in the method, and/or instructions with respect to the diagnosis of endometriosis based on the detected amount of CD200L in the biological sample as detailed above.

DEFINITIONS

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "an antibody" should be understood to present certain aspects with one substance or two or more additional substances.

In embodiments comprising an "additional" or "second" component, such as an additional or second antibody, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

EXAMPLES

Example 1

The following examples illustrate the scope of the invention. Specific elements of the example are for descriptive purposes only and are not intended to limit the scope of the invention. Those skilled in the art could develop equivalent methods and utilize comparable materials that are within the scope of the invention.

Experimental Methods and Procedures

Patient materials: Archived normal pre-menopausal uteri from women or matched hysterectomy specimens and simultaneously resected peritoneal endometriotic implants were used. Hysterectomy specimens from women without endometriosis were used as controls. Table 1 summarizes patient details. The study was approved by the Hamilton Integrated Research Ethics Board.

TABLE 1

Properties of patients that were studied using immunohistochemistry

| Designation | Age | Symptoms requiring hysterectomy | Cycle phase | Adenomyosis |
|---|---|---|---|---|
| EM1 | 37 | pelvic pain + dyspareunia | Proliferative | No |
| EM2 | 41 | pelvic pain + dyspareunia + fibroids | Proliferative | No |
| EM3 | 41 | pelvic pain + dyspareunia | Secretory | No |
| EM4 | 40 | pelvic pain | Secretory | No |
| EM5 | 47 | pelvic pain + menorrhagia + fibroids + anterior serosal adhesions | Secretory | Yes |
| NE1 | 45 | uterine prolapsed with incontinence | Secretory | No |
| NE2 | 41 | menorrhagia | Secretory | No |
| NE3 | 32 | dysmenorrhea + small fibroid | Proliferative | No |
| NE4 | 40 | symptomatic fibroids | Proliferative | No |

An additional cohort of women diagnosed with laparoscopically-proven endometriosis (EM) and a control group (NE) composed of women without evidence of endometriosis (but pelvic pain) were recruited and consented to providing endometrial biopsy tissue and a peripheral blood plasma and serum sample. The plasma samples were used in a previous study showing increased brain-derived neurotrophic factor (BDNF) in endometriosis (Wessels et al., 2016). The mean (±standard deviation) age for women with endometriosis (34.5±6.71) did not differ from women in the control group (35.4±8.29). All study participants reported regular menstrual cycles and current medication use reported by study participants excluded ovarian suppressing medications. All participants were self-reported non-smokers.

Antibodies and Immunohistochemistry (IHC) staining: The method is described in detail in Clark et al. (2017). Briefly, immunostaining was performed in the Department of Pathology's Immunohistology Facility in the Michael DeGroote Centre for Learning and Discovery at McMaster University using 4 µ sections cut from paraffin blocks affixed to positively-charged slides. In the initial set of IHC studies antigen recovery was done by heating in EDTA buffer pH8 (for anti-CD200 and anti-CD200R) or citrate buffer pH 6 (for Ki67) in a Biacore Digital Decloaking Chamber using factory settings. Rabbit anti-human CD200 (RB846) serum and pre-immune control rabbit serum a kind gift from Dr. R. Gorczynski and described in detail elsewhere was used at a $\frac{1}{1000}$ dilution (Clark et al., 2017). In particular, immunohistochemical staining for human CD200 employed a rabbit polyclonal antibody raised against the extracellular V+C regions of CD200 that were genetically attached to the gene sequence coding the AA of the Fc fragment of IgG in order to render the CD200 soluble. Rabbit anti-Fc activity was absorbed out using an anti-Fc column. It is believed that this antibody reacts with AA sequences encoded by exons 1, 2, and 3. We also used an anti-CD200R raised against a 150-200 AA fragment of CD200R2 (Uniprot/UniParc accession ID Q6Q8B3-1) coupled to KLH and antigen-affinity purified (Antibodies-online ABIN1715098, anti-CD200R1L). According to the published Antibodies-online specifications, in Western blots this antibody detected a strong 37 kD and a weaker 30 kD band compatible with classical CD200R1 (325 AA) and CD200R1L (CD200R2) (271 AA) absent glycosylation respectively. There are a number of shared amino acid (AA) sequence regions, one as long as 46 AA, between CD200R1 and CD200R1L (CD200R2) that would make it likely for a polyclonal antiserum to react with both receptors (Wright et al., 2003). For this reason, we have used the CD200R designation throughout this document except where classical CD200R1/R1L are indicated.

In the second set of studies, the slides were stained for CD200L using rabbit antigen-affinity purified antibody for AA 45-95 of the conical sequence of CD200 canonical isoform a, (Uniprot/UniParc accession ID P41217-1) (Antibodies Online ABIN761396) and for CD200S using rabbit anti-human CD200 antibodies generated against the amino acid (AA) 170-220 sequence of the canonical isoform a, P41217-1 (Antibodies-online, ABIN318966). Rabbit anti-KLH antibody (Antibodies-online, ABIN401183) was used as a control. All antibodies were diluted 1:200 in Power Vision IHC Super Blocker (Leica) prior to staining. Slides were stained using the Bond Polymer Refine Detection kit (Leica). Stained slides were digitally scanned and analyzed using Imagescope (Leica), and photographed at 200× and 400×. Digital colour photomicrographs at 400× were taken using Imagescope from 11-13 different areas/specimen beginning at the epithelium and extending to glandular regions in the luminal half of the endometrium. Each CD200S$^+$ cell (nucleus+intracellular staining) was numbered so that no cell was missed and no cell was double counted. Using the scale bar of 50 µm, the area represented 0.0335 mm$^2$, and given a uniform 4 µm thickness of each section, a unit volume of 1340 µm$^3$ or 0.000134 mm$^3$. The CD200S$^+$ cell count reflects cell number per unit volume. The number of positive cells in 11-13 photomicrographs was used to calculate the mean and sem number of cells per unit volume for each secretory phase endometriosis and non-endometriosis cases.

The slides were scanned using Imagescope and photographed at 10×, 40×, 100× and 400× into jpeg files. Image analysis was done using NIH Image J 1.4 software. Briefly, using Image J software, 5 to 6 semi-rectangular areas of the endometrium at 10× magnification (or foci of specific interest at higher power magnification) were outlined using the drawing tool (which allows precise inclusion of irregularly shaped borders) so as to provide intensity data in pixels from which a mean and standard error of the mean could be calculated. The blue intensity with the control antibody was subtracted from the red-brown+blue intensity in each semi-rectangle with the corresponding antigen-specific stain.

qRT-PCR analysis: Samples of eutopic endometrium were obtained by pipelle biopsy during laparoscopic surgery for chronic pelvic pain and suspicion of endometriosis. Study participants were assigned to control (no endometriosis) or cases (endometriosis) based on evidence of endometriotic lesions noted by the surgeon in the operative report and confirmation by histopathology in the pathology report. Samples were transferred to the lab on ice where they were minced and suspended in RNA later (SigmaAldrich Chemical Co. Oakville, ON) for 24 hr at 4° C. and then transferred for storage 85° C. until required for analysis.

Sample RNA was nano-dropped and reverse transcribed into cDNA using the iScript cDNA Synthesis Kit (Bio-Rad). Each RT reaction consisted of 4ul of 5×iScript reaction mix. 1 ul of iScript reverse transcriptase, and variable volumes of Nuclease-free water and RNA template to produce a cDNA volume of 200 ng. Each reaction was heated to 25° C. for 5 minutes, 42° C. for 30 minutes and finally 85° C. for 5 minutes. Real-time qPCR was completed using the CFX96 Touch Real-Time PCR Detection System (BioRad). Each sample was analyzed in triplicate on a 384-well plate. Each well contained a reaction mixture including 2.5 uL of sample template cDNA, 1.5uL RNAse-free water, 0.5uL of the target Forward and Reverse Primer** and 5uL of SYBR Green. Each 384-well plate was heated to 95° C. for 15min, followed by 45 cycles at 94° C. for 10 seconds, 60° C. for 10 seconds and 72° C. for 10 seconds. This was followed by one cycle for melting curve acquisition.

ELISA analysis: An initial set of studies was conducted using R&D Systems' ELISA assay (DuoSet, Catalogue #D42724) according to the manufacturer's specifications. Ninety-six well ELISA plates were coated with their proprietary mouse monoclonal anti-human CD200 capture antibody, washed, and incubated with serial dilutions of the sCD200:Fc control antigen or with test peripheral blood serum from non-endometriosis controls (NE) or endometriosis patients (EM) during the menstrual phase. The sera were tested at ½, ¼, ⅛, ⅙, and 1/32 dilutions to be sure the result was not affected by inhibitors in the serum. Inhibitors in serum may include, but are not limited to, soluble CD200R1 to which CD200L binds, IgG to which sCD200 may bind, CD200S which may bind to the capture antibody and impede binding of CD200L. A second set of studies (see Example 2) was done using serum samples from endometriosis patients EM (N=13) and non-endometriosis patients (with pelvic pain) NE (N=10) cases using a more sensitive commercially available RayBioTech sandwich Human CD200 ELISA kit (ELH-CD200, RayBioTech, Norcross, Ga.). Each individual plate assessed sCD200 concentrations of four to five EM and three to four NE during either the secretory, menstrual, or proliferative phase. The sera were tested at ½, ¼, ⅛, ⅙, and 1/32 dilutions to be sure the result was not affected by inhibitors in the serum. Inhibitors in serum may include, but may not be limited to, soluble CD200R1 to which CD200L binds, IgG to which sCD200 may bind. Duplicate at a 1 in 2 dilution gave optimal results (Wong et al., 2016). Stage in the menstrual cycle was determined by the time elapsed from date of the last menstrual period to the date of sample collection. The optical density was measured using a BioTek Utility of Synergy H4 Hybrid Multi-Mode Microplate Reader (BioTek, Winooski, Vt.) at a wavelength of 450 nm. CD200 concentrations were determined from a standard curve using different concentrations of the CD200 standard (P41217.3) and the resulting optical density values (OD) were fitted to a second order polynomial $y=ax^2+bx+c$ model as described by Herman et al. (2008) using Microsoft Excel. Here y=OD and x=soluble CD200 concentration (including zero values). The concentration of sCD200 in individual test wells based on the OD value was determined from the formula sCD200 pg/ml= $(-b+SQRT(b^2-4a(c-OD)))/(2a)$.

Statistics: The data was initially analyzed using Prism 8 (GraphPad Software San Diego, Calif., USA) and included tests for normality and lognormal distribution. In all cases except one where n was sufficient, a lognormal distribution was confirmed, and the data are shown in figures on a log scale along with the geometric mean. The mean and standard error of the mean (SEM) for ln transformed data was used to calculate p using the parametric Student't test. When neither a normal nor lognormal data distribution occurred, the Fisher's Exact test was used. In all comparisons, p values were confirmed using the non-parametric Wilcoxon rank sum test and precise p values estimated using the online calculator of Navendu Vasavata 2016 (astatsa.com). Because the initial IHC study of CD200 expression in endometriosis indicated increased production of CD200 in the secretory phase and not proliferative phase of the menstrual cycle, with no change in staining for CD200R (which included CD200R1 and CD200R2) this a priori knowledge eliminated the need for a Bonferonni correction that would have required for multiple tests (N) of significance a p value≤0.05/N (at the risk of false negatives, a type II error). In all cases, $p<0.05$ was considered to indicate statistical significance.

Results

CD200 and CD200R are Detected by Immunohistochemistry in Peritoneal Endometriosis Deposits in Both Proliferative and Secretory Phase of the Menstrual Cycle.

FIG. 1 shows staining for CD200 and CD200R in peritoneal endometriosis deposits at 100× magnification. Dark foci of $CD200^+$ and $CD200R1^+$ deposits in endometrial epithelium forming cyst walls and in the stroma were evident in stroma, $CD200^+$ and $CD200R^+$ acellular material within cysts was compatible with shed/soluble membrane. A deposit in myometrium in EM5 (adenomyosis) was also positive for both markers. Note lack of staining of the myometrium. There was no striking difference between staining of ectopic deposits in the proliferative phase of the menstrual cycle compared to the secretory phase. These data raised the question, as to whether or not uterine endometrium from these same cases showed similar staining, and if so, was it different from staining in the endometrium of patients with no evidence of endometriosis (NE).

CD200 and CD200R Staining is Present in Proliferative Phase Endometrium from Both Non-Endometriosis Controls (NE) and Endometriosis Patients (EM)

Figure 2:
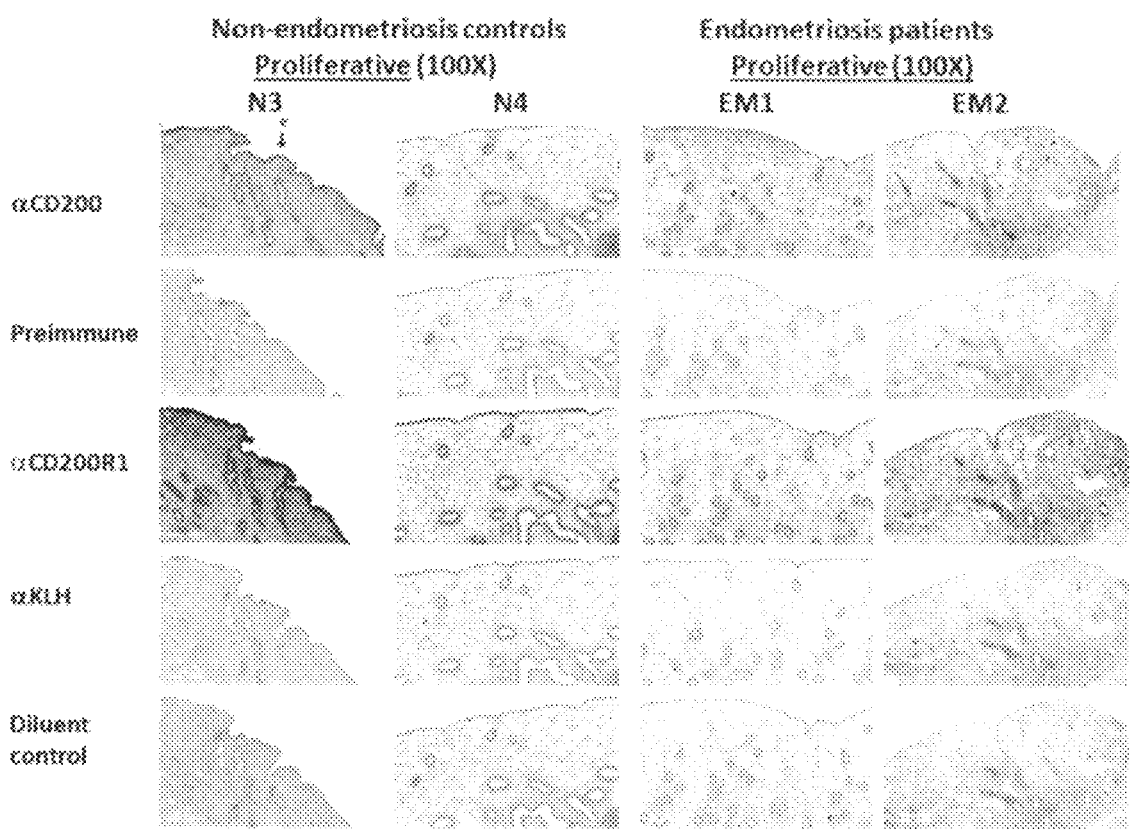
FIG. 2 depicts the proliferative phase Endometrium of patients with endometriotic deposits (EM) shown in FIG. 1, compared to the proliferative phase endometrium from control women with no evident endometriosis (NE) (100×magnification). e=luminal epithelium.

FIG. 2 shows that CD200 and CD200R staining was present in proliferative phase endometrium from both 2 non-endometriosis controls (NE) and 2 endometriosis patients (EM) at 100× magnification. The luminal epithelium stained as well as the epithelium of endometrial glands which in some sections can be seen communicating with the uterine lumen. There was also scattered dark spot staining in stroma which is not as well defined as in epithelium. Note the pre-immune and anti-KLH control antibody as well as diluent control (no antibody used) provides the comparator defining absent staining.

CD200 and CD200R Staining is Present in Secretory Phase Endometrium from Both Non-Endometriosis Controls (NE) and Endometriosis Patients (EM)

Figure 3:
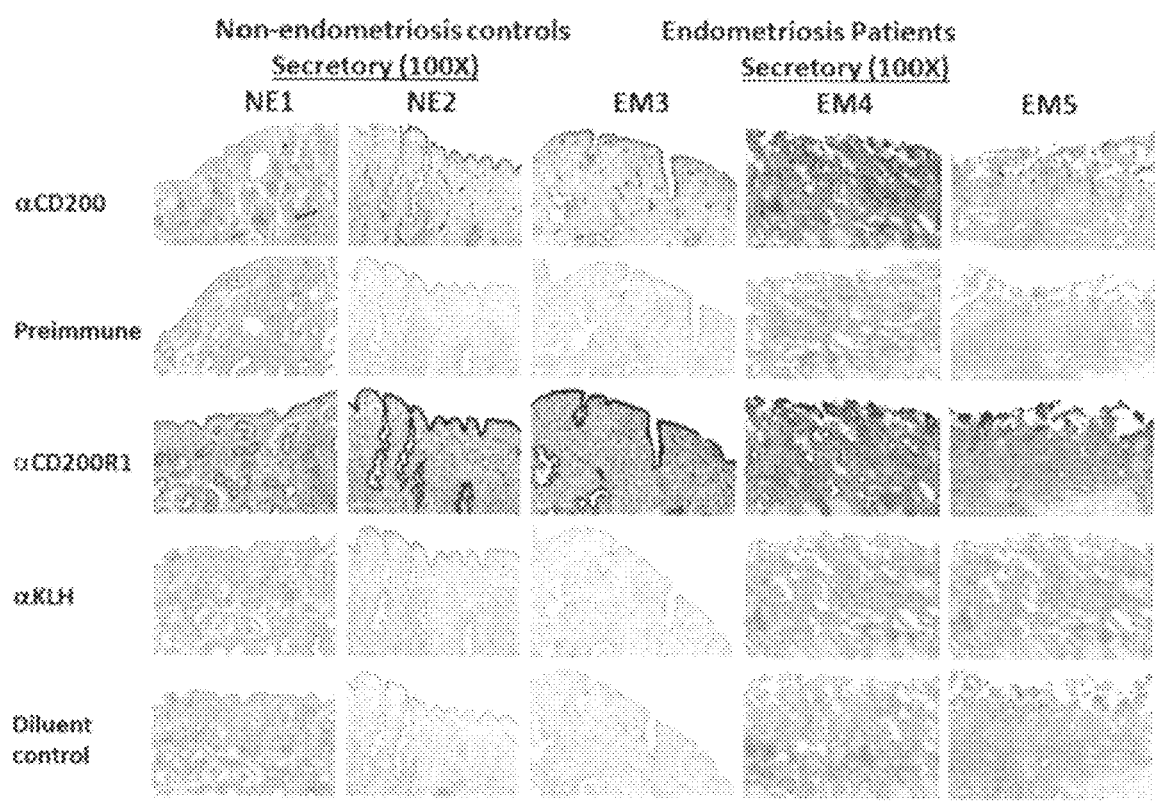
FIG. 3 depicts the secretory phase Endometrium of patients with endometriosis (EM) compared to the secretory phase endometrium from control women with no evident endometriosis (NE) (100× magnification).

FIG. 3 shows 100× magnification photomicrographs similar to FIG. 2 of endometrium in uterine sections done in the secretory phase of the menstrual cycle from 2 control patients who did not have endometriosis and 3 with endometriosis. Again the epithelium of glands is stained for CD200 and CD200R. More striking staining for CD200 and CD200R was noted in EM4 and EM5 which appear to be late in the secretory phase as superficial endometrium is beginning to slough. At this magnification, details of variable staining in stroma is less clear than in epithelium. Staining of CD200 and CD200R is also present in acellular material within the lumens of endometrial glands.

CD200 and CD200R Increased in Luteal Phase Endometrium of Patients with Endometriosis The 100× magnification images in FIGS. 1-3 provide a general picture of staining for CD200 and CD200R, but as already pointed out, detailed information about staining in stroma was minimal. Therefore 400× photomicrographs were examined.

Figure 4:
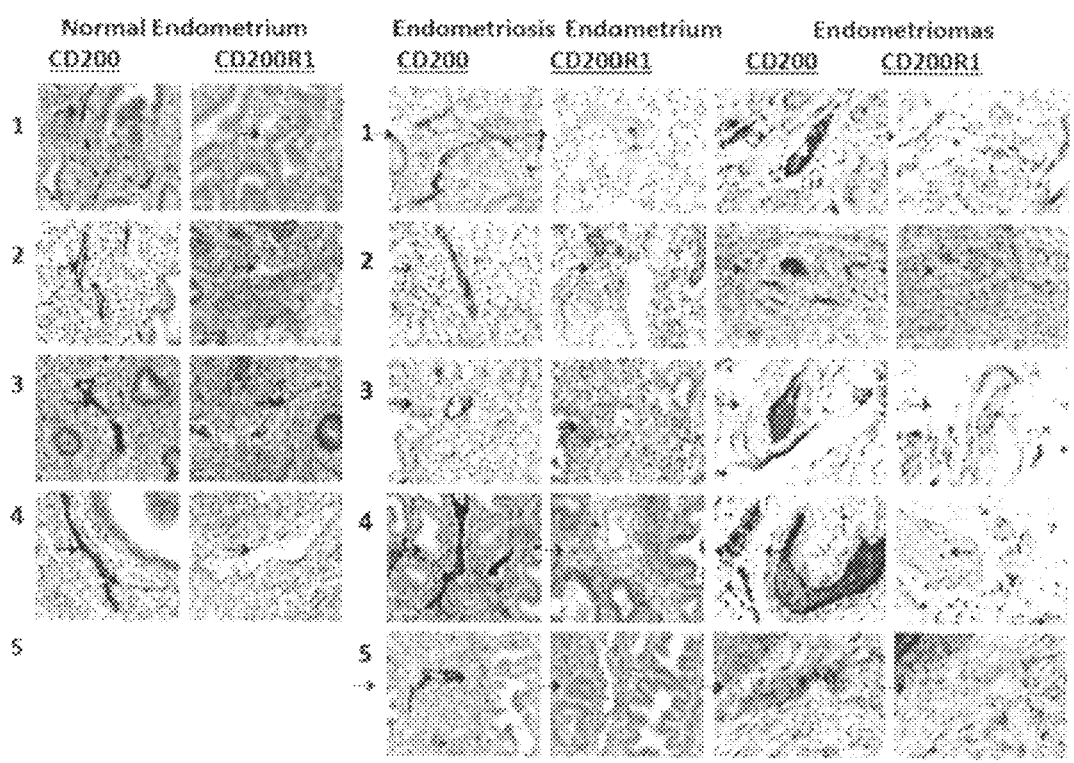
FIG. 4 is a High power (400× magnification) view of endometrium of normal NE patients 1, 2, 3, and 4, and endometriosis EM patients 1, 2, 3, 4, 5 and corresponding peritoneal endometriotic deposits from each EM patient. Arrows point to notably dense (dark) staining of CD200.

FIG. 4 shows the result with 4 control patients and 5 endometriosis patients including the proliferative and secretory phases of the cycle. It can be seen that both glandular epithelium and some cells in the stroma stained for both proteins, but staining appeared to be increased in the luteal phase endometrium of patients with endometriosis particularly in the epithelial of endometrium about to be shed by menstruation. $CD200^+$ and $CD200R^+$ acellular material was frequently present in endometrial gland lumens. Staining is quantified in Table 2. FIG. 4 left set of 2 panels shows CD200 staining of glandular epithelium of NE cases and staining of channels in stroma that appear to be venules containing erythrocytes or lymphatics where erythrocytes were not seen: in ¾ cases, staining for CD200R was undetectable. In the middle set of 2 panels from EM cases, a similar result for CD200 staining was noted in 5/5 cases, and in only 1/5 cases (#4) was there weak staining for CD200R. In the right set of 2 panels, 5/5 endometriotic deposits showed dense staining of the contents of venules with possibly weak staining in the lumen in 1/5 (#5) and weak venule wall staining in 1/5 (#3). Based on staining intensity, CD200 was >>> and CD200R staining.

lower CD200R staining. Due to the small sample size, none of the differences achieved statistical significance.

Analysis of Luminal Portion of Endometrium

As it is the luminal component between the basal layer that abuts myometrium and the luminal surface that will be shed and pass in a retrograde manner into the peritoneal

TABLE 2

Quantitative analysis of expression of CD200 and CD200R1L in full thickness endometrium of normal (NE) and endometriosis (EM) women

| | Proliferative Phase | | | Secretory Phase | |
|---|---|---|---|---|---|
| | CD200[a] | CD200R | | CD200 | CD200R |
| NE3 | 17.9 ± 1.2 (5)[ab] | 38.9 ± 2.8 (5) | NE1 | 11.8 ± 2.5 (5) | 19.8 ± 1.0 (5) |
| NE4 | 8.5 ± 1.0 (5) | 11.7 ± 0.5 (5) | NE2 | 17.6 ± 1.7 (5) | 30.6 ± 1.5 (5) |
| μ[c]= | 13.2 ± 1.5 | 25.3 ± 2.8 | | 14.7 ± 3.0 | 25.2 ± 1.8 |
| EM1 | 9.4 ± 0.5 (5) | 12.7 ± 1.6 (5) | EM3 | 16.9 ± 1.8 (5) | 24.9 ± 1.8 (5) |
| EM2 | 16.5 ± 2.4 (5) | 20.8 ± 1.4 (5) | EM4 | 23.9 ± 1.6 (5) | 25.0 ± 1.3 (5) |
| | | | EM5 | 8.0 ± 1.9 (5) | 20.6 ± 1.9 (5) |
| μ[c]= | 13.0 ± 2.5 | 16.8 ± 2.1 | | 16.3 ± 2.2[d] | 23.5 ± 2.1 |

Figure 5:
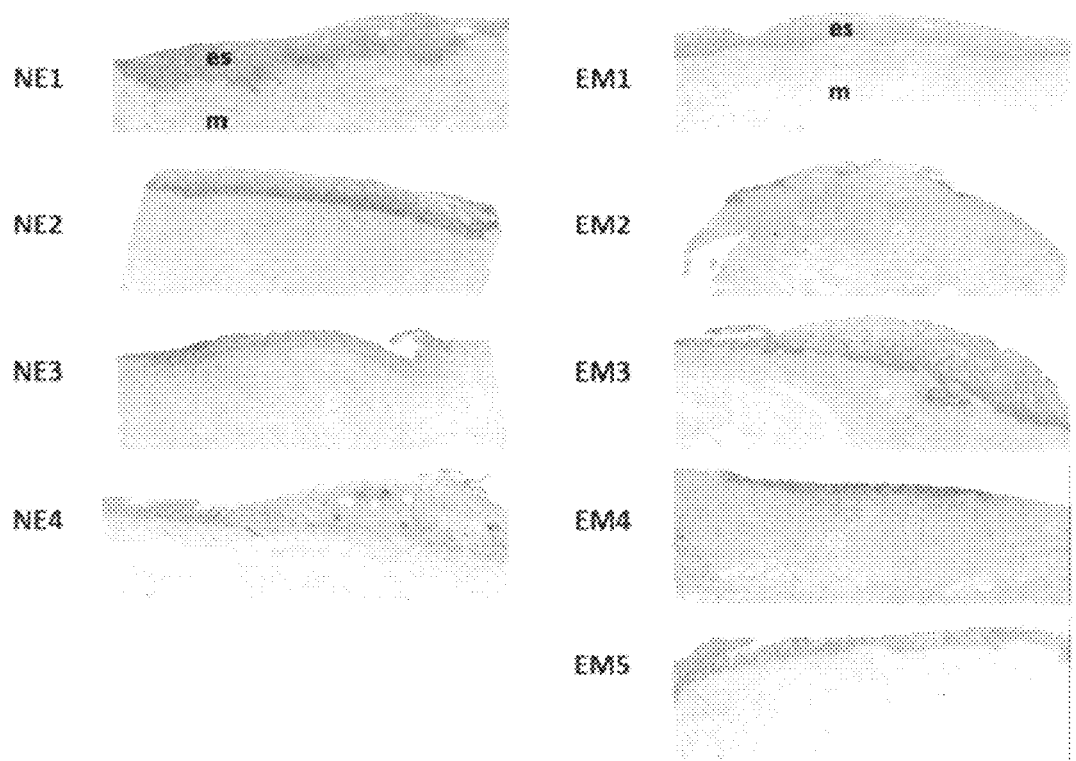
FIG. 5 shows low power 10× views of full thickness sections of uteri with endometrial stripe (es) and myometrium (m).

[a]anti-CD200 $^{1}/_{1000}$ intensity mean and 1 sem after subtraction of pre-immune control $^{1}/_{1000}$
[b]parenthesis show number of areas measured.
[c]mean ± 1 sem.
[d]the mean value of 16.3 ± 2.2 in the EM secretory phase group was greater than in the proliferative phase and in NE secretory and proliferative phases but this trend did not achieve statistical significance t = 1.01, 1.16, 0.43 respectively.
Quantification of CD200 and CD200R in endometrial stripes of whole uterus images FIG. 5 shows low power (10× magnification) whole uterus images. Using Image J software, the endometrial stripe (stained with anti-CD200) was divided into 5-6 adjacent semi-rectangular areas and red versus blue staining intensity was measured. In the black and white version of the figures, red is dark and blue is white. The result for full thickness endometrium is shown in Table 2. The data for CD200 represents the number of pixels with anti-CD200 minus the number of pixels with pre-immune control serum, and for CD200R, the number of pixels with anti-CD200R minus the number of pixels with control anti-KLH. The mean and I standard error of the mean (sem) was determined using the 5-6 semi-rectangular areas that encompassed the entire endometrial stripe. The mean and 1 sem for each group of 2 or 3 patients was then calculated. There was more anti-CD200R staining than anti-CD200, and a slight trend to more CD200 in the secretory phase, although the latter was more evident in the proliferative phase EM group, due to cavity, that component of the endometrium is potentially of greater importance, and so a similar analysis of the luminal ½ of the endometrium abutting the lumen was done and is shown in Table 3. As shown, the result is similar to the outcome in FIG. 2 except for a more prominent increase in CD200 in EM secretory phase. Indeed, in FIG. 3, in late phase endometrium the staining intensity was striking. However, due to small sample size, the increase in CD200 staining did not achieve statistical significance.

TABLE 3

Quantitative analysis of expression of CD200 and CD200R in inner (luminal) half of endometrium of normal (NE) and endometriosis (EM) women

| | Proliferative Phase | | | Secretory Phase | |
|---|---|---|---|---|---|
| | CD200 | CD200R | | CD200 | CD200R |
| NE3 | 19.8 ± 2.2 (5) | 47.8 ± 4.6 (5) | NE1 | 10.5 ± 3.2 (5) | 20.0 ± 1.2 (5) |
| NE4 | 8.9 ± 1.6 (5) | 12.9 ± 0.6 (5) | NE2 | 21.3 ± 1.5 (5) | 35.0 ± 1.2 (5) |
| μ= | 14.4 ± 2.7 | 30.4 ± 4.6 | | 15.7 ± 1.7 | 27.5 ± 1.7 |
| EM1 | 10.4 ± 1.3 (5) | 11.2 ± 1.4 (5) | EM3 | 18.0 ± 2.3 (5) | 28.5 ± 2.7 (5) |
| EM2 | 16.6 ± 4.8 (6) | 25.5 ± 2.4 (6) | EM4 | 27.2 ± 2.6 (5) | 28.4 ± 1.5 (5) |
| | | | EM5 | 11.3 ± 1.6 (5) | 20.6 ± 1.5 (5) |
| μ[a]= | 13.5 ± 5.0 | 18.4 ± 2.8 | | 18.8 ± 2.6[b] | 25.8 ± 2.4 |

[a]Mean and 1 sem.
[b]The mean CD200 staining of 18.8 ± 2.6 from 3 EM secretory phase cases versus 13.5 in EM proliferative phase and 15.7 ± 1.7 NE secretory and 14.4 ± 2.7 NE, proliferative phase groups achieved t = 0.94, 1.08, 1.47 respectively.
Quantification of staining in walls of venules and lymphatic channels in endometrial stroma To further investigate the staining of non-epithelial stromal venules and lymphatic channels noted in FIG. 4, Image J analysis was done. Venules were identifiable by the presence of intra-luminal erythrocytes. It was difficult to find identical areas in the negative isotype control-stained sections to compare to the stained tissues, but as control antibody staining intensities are usually quite similar for anti-CD200 and anti-CD200R, and anti-CD200R staining of venule/lymphatic walls was similar to adjacent stroma, the value of CD200-CD200R staining intensity (Δ) was determined. For 4 normal patient endometrial, Δ was 51.2±7.1 (8 measurements) and for 5 endometriosis patients, Δ was slightly greater at 59.5+8.3 (10 measurements), which was not statistically significant. In endometrium, unlike in endometriomas, there was no CD200 staining within the vascular lumens.

Expression of both CD200 and CD200R were detected in endometriotic deposits and in a deposit of adenomyosis. In peritoneal deposits, small areas compatible with venules and lymphatic channels that were intensely positive for CD200 lacked CD200R expression, but as epithelial cysts formed, CD200R was detected in the epithelium and was usually>CD200 staining intensity. Further, both CD200 and CD200R were detected in the proliferative and secretory phase endometrium of these patients. In full thickness endometrium, Table 2 shows similar values for CD200 and CD200R comparing endometriosis patients to controls. CD200 was lower in the proliferative phase (16.8±2.1) but this was not statistically different from normal control (25.3±2.8) (t=2.41, P<0.1 but in the secretory phase, EM patient, CD200 staining intensity was greater than in the proliferative phase. However, the difference was not statistically significant. In NE patients, CD200 did not increase in the secretory phase, and was similar to the mean EM proliferative phase value.

6. Type A deposits were linear cellular walls with no evident lumen, whereas B showed a cellular wall and lumen containing erythrocytes or neutrophils and sometimes some fluid phase staining. Type C deposits were larger accumulations with a CD200$^+$ fluid phase±wall staining, and sometimes erythrocytes were present (but were excluded in the Image J scoring). For purposes of analysis of conduits containing sCD200$^+$ type B vessels where there was obvious cell-free CD200$^+$ fluid, these were denoted B-C and ultimately grouped with type C deposits.

It can be seen from the tabulation that the frequency of Type C accumulations was significantly greater (P=0.000006, by Fisher's Exact test) in the secretory phase EM tissues compared to secretory phase NE tissue, and in contrast to no evident difference comparing NE to EM in proliferative phase endometrium. Using Type C deposits, for proliferative endometrium the product of intensity×area× number of deposits per case averaged 2241±726 for NE versus 391±129 for EM (P+ NS by Student's t test), whereas in secretory endometrium it was 1748.9±187.1 for EM versus 186.7 in NE (no sem calculated as only 1 value). The standard deviation of 1748.9 was 560.248 so that 186.7 was P<0.00265 below the EM mean (z=1561.8/560.248=2.787). The higher sCD200 value in secretory phase EM vessels contrasted with the proliferative phase result where the NE value was>than the EM value. The data were compatible with increased accumulation of sCD200 in the vascular/ lymphatic lumens in secretory phase EM endometrium.

TABLE 4

Quantitative measurement of focal stromal CD200 staining

| | PROLIFERATIVE | | SECRETORY | |
|---|---|---|---|---|
| | NE3 (19) | NE4 (18) | NE1 (20) | NE2 (21) |
| μ ± sem | 56.89 ± 3.33 | 38.34 ± 3.01 | 59.57 ± 3.33 | 72.79 ± 4.31 |

| | PROLIFERATIVE | | SECRETORY | |
|---|---|---|---|---|
| VESSEL | NE3 | NE4 | NE1 | NE2 |
| A | 3 | 1 | 13 | 9 |
| B | 12 | 4 | 6 | 12 |
| C | 4 | 13 | 1 | 0 |

| | EM1 (20) | EM2 (11) | EM3 (41) | EM4 (45) | EM5 (27) |
|---|---|---|---|---|---|
| μ ± sem | 54.5 ± 3.15 | 76.0 ± 7.40 | 73.2 ± 3.51 | 74.0 ± 2.09 | 62.1 ± 4.30 |

| | EM1 | EM2 | EM3 | EM4 | EM5 |
|---|---|---|---|---|---|
| A | 6 | 0 | 5 | 20 | 12 |
| B | 9 | 7 | 13 | 17 | 5 |
| C | 5 | 4 | 22 | 8 | 10 |

| | A + B | C | | A + B | C |
|---|---|---|---|---|---|
| NE3 + 4 | 20 | 17 | NE1 + 2 | 40 | 1 |
| EM1 + 2 | 22 | 9 | EM3 + 4 + 5 | 72 | 40 |
| | Exact P = 0.12 | | | Exact P = 0.000006 | |

Figure 6:
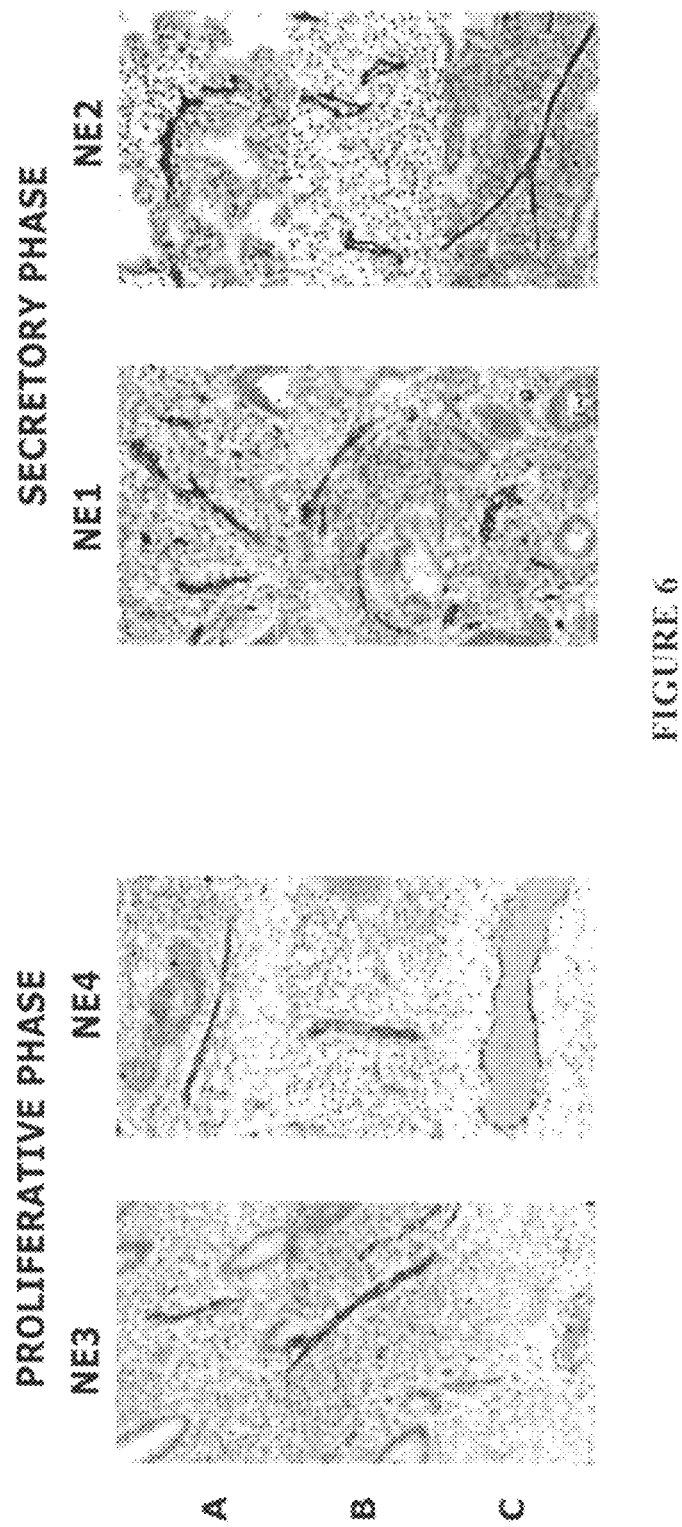
FIG. 6 shows 400× photos of different types of stromal deposits (A, B, or C) in normal tissue (NE) and endometriosis tissue (EM) from the proliferative phase and secretory phase.

Table 4 shows the result of analysis of endometrial stromal deposits large enough for Image J quantitation according to the classification shown in FIG. 6. The Image J signal with anti-CD200 had the background staining with pre-immune rabbit serum subtracted. While in the secretory phase, the mean EM staining was greater than in NE, the difference was not statistically significant. On further analysis, stromal deposits could be subdivided as shown in FIG.

Collette et al. (2004) have reported elevation of endometrial proteolytic activity in normal and endometriosis patient endometrium, with a peak in the secretory phase, and although EM values from individual patients shows a 30% overlap of the NE range, increased cellular expression of CD200 combined with increased proteolytic activity can explain intense intralumenal staining of sCD200 in vascular/ lymphatic structures. Increased accumulation could also occur due to reduced blood flow which has been documented in the endometrium of infertile patients (and EM causes infertility). Elevated sCD200 and CD200+ cells in menstrual blood would be a logical prediction.

CD200 mRNA Levels Significantly Increased in Secretory Phase Endometrium

To determine if the accumulation of sCD200 in the venules/lymphatics of secretory endometrium, particularly in the basal zone, was due to increased generation of sCD200 by matrix metalloproteinases cleaving surface CD200 (Wong et al., 2016; Collette et al., 2004) or due to increased synthesis of CD200, qRT-PCR analysis of stored whole endometrial samples was carried out. The primers used included:

```
CD200 F
                                            (SEQ ID NO: 1)
5'-acc cag gat gaa aga gag ca-3'

CD200 R
                                            (SEQ ID NO: 2)
5-tat agg cag gct gga tca cc-3'

CD200R1 F*
                                            (SEQ ID NO: 3)
5'-cca ttt gac tgg caa-3'

CD200R1 R*
                                            (SEQ ID NO: 4)
5'-gca gcc att gac ttt caa ca-3'

CD200R2 F
                                            (SEQ ID NO: 5)
5'-caa ggc agt tac agg gaa gc-3'

CD200R2 R
                                            (SEQ ID NO: 6)
5'-gcc agt caa atg gga gac at-3'
*Designed at the University of Toronto (University
Health Network) and is published in the public
domain.
```

The amplification of CD200, CD200R1, and CD200R2 mRNA in the qRT-PCR was expressed as fold increase over GAPDH control provided by a Qiagen QuantiTect Primer Assay (QT007924) which detects GAPDH transcripts NM_0011256799, NM_002046, NM_001289745, and NM_001289746. The primer sequences are proprietary, and include primers for GAPDH (QT007924) as follows:

```
GAPDH F
                                            (SEQ ID NO: 7)
5'-tca acg acc act ttg tca aac ctc a-3'

GAPDH R
                                            (SEQ ID NO: 8)
5'-gct ggt ggt cca ggg gtc tta ct-3'.
```

Figure 7:
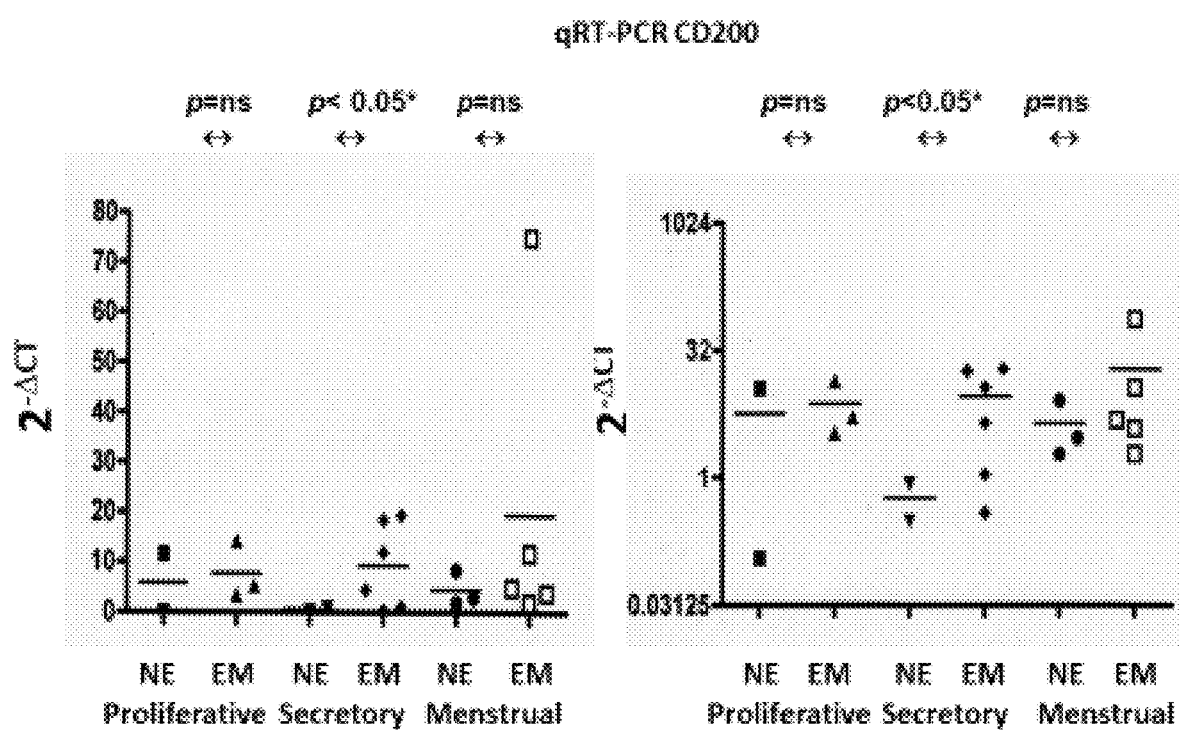
FIG. 7 shows Quantitative real-time polymerase chain reaction (qRT-PCR) values for proliferative, secretory, and menstrual phase endometrial biopsy tissue from patients without endometriosis (NE) and with endometriosis (EM) are displayed on a $\log_2$ scale. The data points represent fold increase with primers for CD200 compared to GAPDH control. The geometric mean is provided in 2 columns comparing EM to NE Above each display is the mean ±1 sem value, and a P value based on Student's t test (2 tail). For the left hand panel, the data represent arithmetic means of the fold increase, whereas for the right hand panel, the mean loge value±1 sem and P value is provided.
Figure 8:
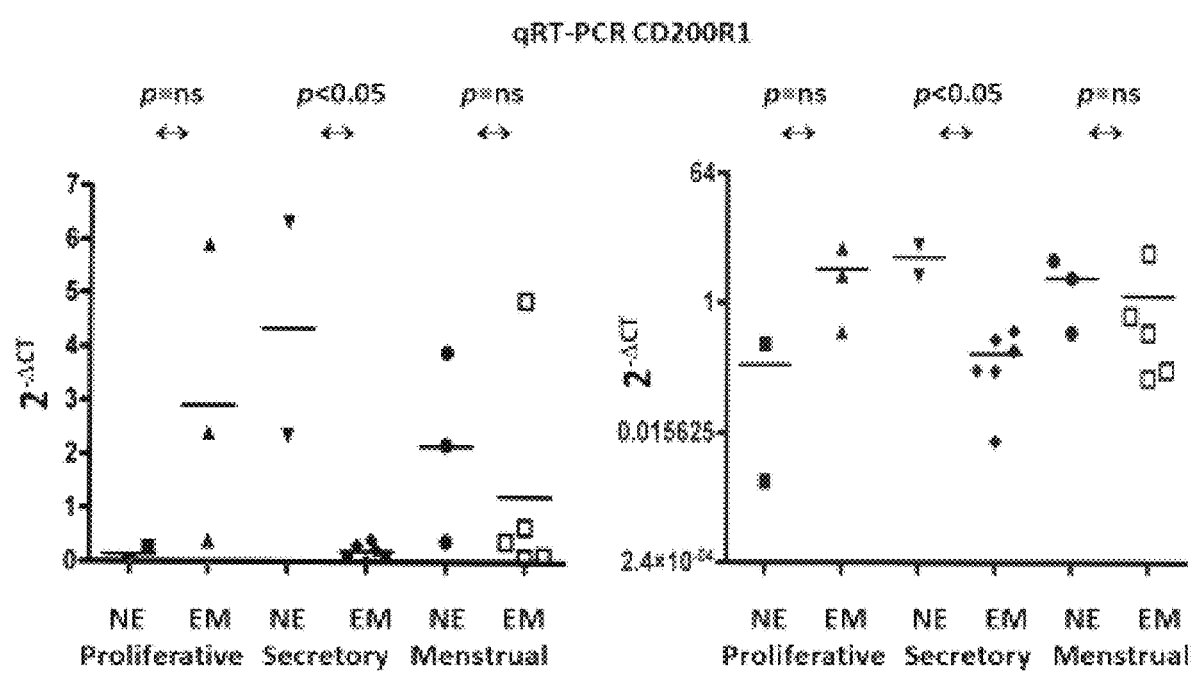
FIG. 8 demonstrates qRT-PCR values as described in FIG. 7 legend, but using primers for CD200R1.
Figure 9:
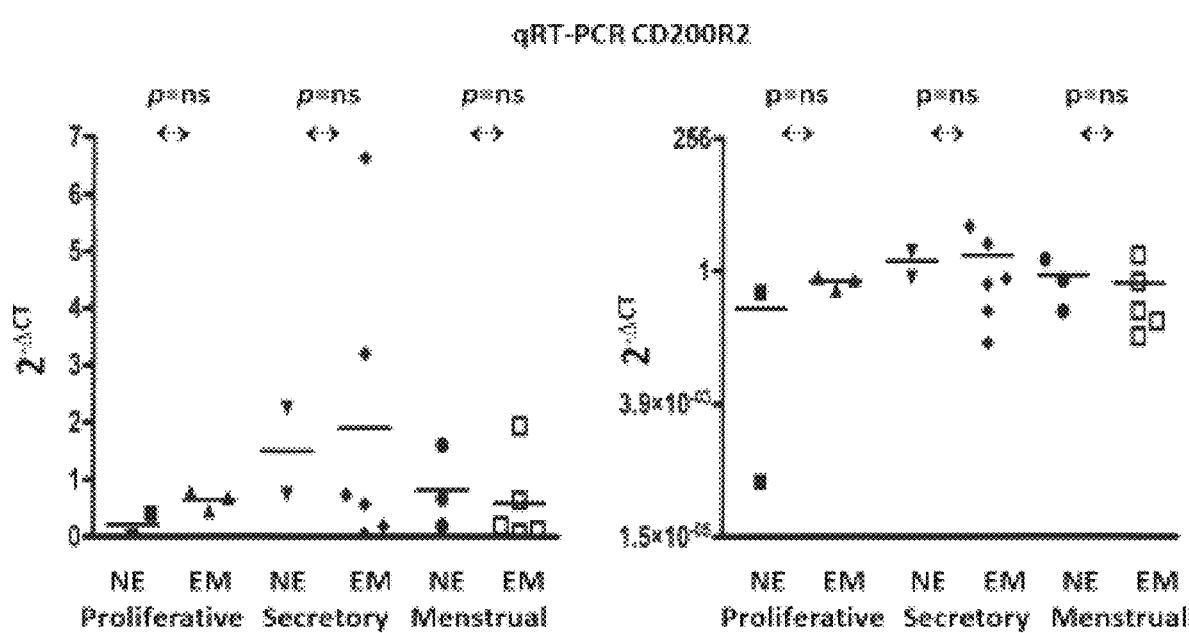
FIG. 9 provides qRT-PCR values as described in FIG. 7 legend, but primers for CD200R2 were used.

To determine if differences in serum sCD200 were related to differences in CD200 production in secretory phase EM cases, mRNA for CD200, CD200R1, and CD200R2 was determined by RT-PCR. It can be seen that comparing CD200 mRNA levels in EM to NE cases in the proliferative phase showed no increase in EM, and that was true when the $2^{-\Delta CT}$ values were also compared. In contrast, in secretory phase endometrium CD200 mRNA levels were significantly increased in EM cases compared to NE controls. This was true also when -ACT values were considered (see FIG. 7A/B). As the null hypothesis was that CD200 levels would not be increased in EM, a 1 tail P value may be used so that P<0.025 was obtained. The overlap of EM with NE values in 2/6 cases could be related to stage of the secretory cycle from which these samples were taken or other technical factors. Even so, increased synthesis of CD200 was present in the EM group compared to NE controls. A similar increase was not seen for CD200R1 or CD200R2 mRNA levels (FIGS. 8 and 9) with this sample size.

The detection of this increase which was not seen in the immunohistochemical (IHC) quantitative analysis of CD200 staining in whole endometrium. This may be for one or more of the following reasons. In preparing the blocks for IHC, during fixation, some soluble sCD200 may have been lost. The polyclonal anti-CD200 antibody used for the initial set of IHC studies was raised against the whole CD200:Fc molecule, and anti-Fc activity was absorbed out. It is now known that there can be a truncated CD200 (called trCD200 or CD200S as distinct from CD200L). CD200S lacks exon 2 determinants of CD200 (Chen et al., 2006; Kobayashi et al., 2016). The primers used for qRT-PCR solely detect CD200L mRNA, whereas the antibody used in the initial set of IHC staining could potentially detect more epitopes of CD200L that the Antibodies Online anti-CD200L, and with the methodology used we cannot exclude the possibility that CD200S might also have been stained. As CD200S stimulates rejection and blocks CD200L, this could result in reduced CD200L bioactivity. It is also noted that the qRT-PCR data in the Figures shows that the amount of CD200R1 was greater than the amount of CD200R2 mRNA in the qRT-PCR analysis of NE endometrium, and in secretory phase EM endometrium, CD200R1 synthesis appeared to decrease resulting in less CD200R1 able to bind to and neutralize CD200L. All of the CD200L epitopes that bind to CD200R1 are in exon 2 (Hatherley et al., 2005), and CD200S is missing exon 2, so which receptor CD200S binds to in order to activate macrophages remains to be determined (Kobayashi et al., 2016).

ELISA Analysis of Peripheral Blood Serum from Secretory Phase NE and EM Cases Demonstrates Increased sCD200 in the Secretory Phase of EM Endometrium.

Figure 10:
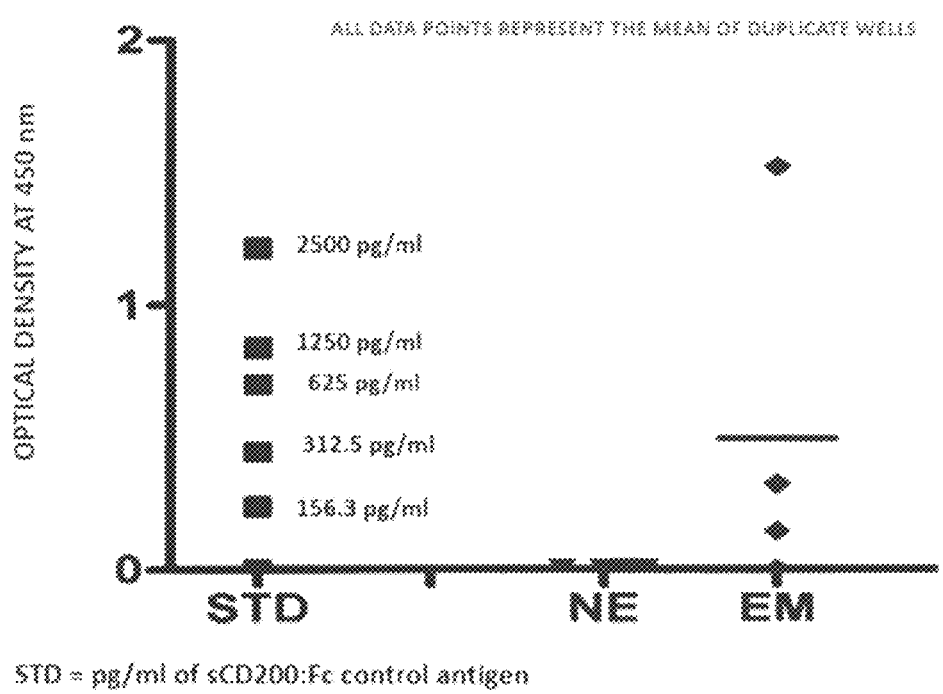
FIG. 10 graphically illustrates the results of a determination of sCD200 in peripheral venous blood serum of patients with endometriosis vs. control samples using R&D Systems ELISA.

The initial ELISA data clearly show elevated blood sCD200 in a significant number of EM samples (see FIG. 10). The data can be converted from OD into pg/ml using a standard curve based on a polynomial model. The R&D Systems ELISA kit exhibits sensitivity as ≥150 pg/ml, and a more sensitive ELISA may have yielded improved results. While R&D Systems indicates their standard curve is linear between 150 pg/ml and 10000 pg/ml, the results obtained did not fit a linear y=ax+b model. Therefore, in FIG. 10, the OD 450 values are given. The background from wells containing diluents alone and no sCD200:Fc or serum was subtracted from all measured OD levels. EM sera obtained from patients in the menstrual phase of their cycle was shown to have elevated levels of sCD200L. Data is shown from the ½ dilution, but a ¼ dilution gave a similar result. In the 4 NE cases, the mean OD above background was 0.0005125+0.000496 (1 sem). Any OD value above 0.00168 exceeded 95% of predicted NE sample values above the mean. As can be seen, the elevated EM case values were above this threshold (1.5165, 0.3260, 0.1476). Results using the more sensitive Raybiotech ELISA are provided in Example 2 below.

Discussion

The presence of very intense deposits of CD200 in venules and veins in peritoneal endometriotic deposits was striking and different from staining of epithelium and non-vascular stromal elements. In the corresponding endometrium there was strikingly positive staining of CD200 in the walls of lymphatics and venules (identifiable by presence of erythrocytes) which implies high levels of soluble CD200

(sCD200) at the capillary level. sCD200 is cleaved from the cell surface and may exert important biological effects at a distance by binding to CD200R+ cells. Nevertheless, the difference in CD200 staining of the walls of lymphatic and venules in endometriosis patients' endometrium was only slightly greater than in normal non-endometriosis control endometrial samples. From FIG. 4, expression of epithelial CD200 at the time of shedding may be quite high. CD200 derived from venular and lymphatic walls is added to menstruated blood. On this basis, quantitative measurement of the concentration of CD200+ cells and sCD200 in menstrual blood provides an estimate of the dose of bioactive CD200 delivered to the peritoneal cavity. That CD200 dose is much greater in EM patients than in NE patients and hence provides a reliable predictor for diagnosing the presence of endometriosis and a predictor of the likelihood of developing endometriosis.

A significant embodiment of the present data is the prediction that the level of sCD200 in menstrual blood and CD200 on menstrual blood cells may provide a more accurate predictor of endometriosis when standardized to 17-β-estradiol levels that modulate CD200 mRNA levels. Different embodiments of the invention have been shown by the above examples. Those skilled in the art could develop alternatives to the methods mentioned above that are within the scope of the invention and defined claims.

Example 2—ELISA Quantitation of sCD200 in Serum

Figure 13:
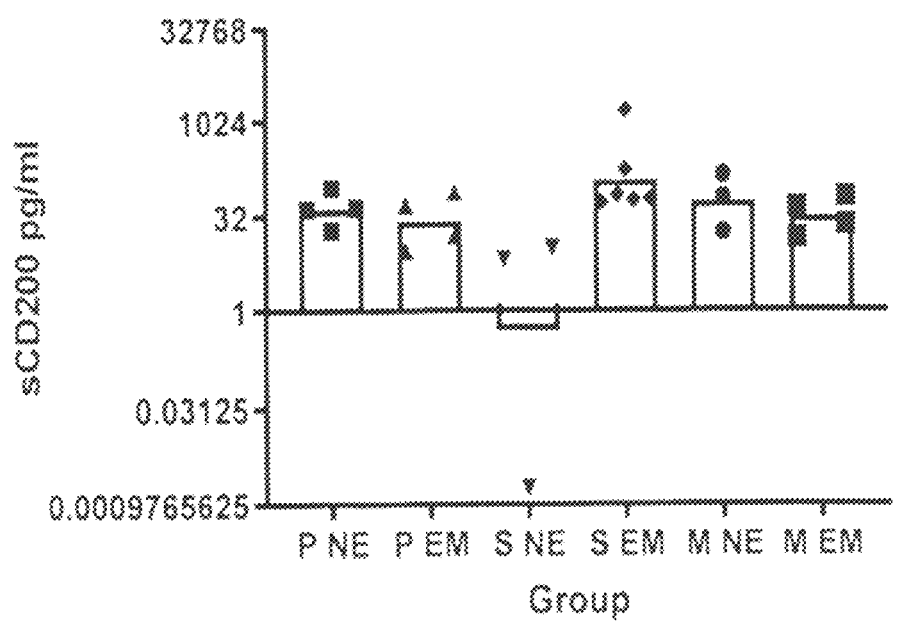
FIG. 13 graphically illustrates levels of sCD200L in peripheral venous blood serum of patients with endometriosis (EM) vs. control (NE) samples using the Raybiotech ELISA for proliferative, secretory, and menstrual phase samples.

Serum samples from endometriosis (EM) (N=13) and non-endometriosis (NE) (N=10) cases were assessed using a commercially available RayBioTech sandwich Human CD200 ELISA kit (ELH-CD200, RayBioTech, Norcross, Ga.) which could detect sCD200 levels as low as 20-30 pg/ml. As described in the method of Example 1, after serial dilution results were examined, a ½ dilution which others have also found optimal was used (Wong et al., 2016) given neat serum can show a prozone effect. Stage in the menstrual cycle was determined by the time elapsed from date of the last menstrual period to the date of sample collection. The optical density was measured using a BioTek Utility of Synergy H4 Hybrid Multi-Mode Microplate Reader (BioTek, Winooski, Vt.) at a wavelength of 450 nm. CD200 concentrations were determined from a standard curve using different concentrations of the CD200 standard (P41217.3) and the resulting optical density values (OD) were fitted to a second order polynomial $y=ax^2+bx+c$ model as described by Herman et al. (2008) using Microsoft Excel (2008). Here y=OD and x=soluble CD200 concentration (including zero values). The concentration of sCD200 in individual test wells based on the OD value was determined from the formula sCD200 pg/ml=$(-b+\sqrt{b^2-4a(c-OD)})/(2a)$.
Results:

The results of a determination of sCD200 in peripheral venous blood serum of patients with endometriosis (EM) vs. control (NE) samples using ELISA for proliferative, secretory, and menstrual phases are shown in FIG. 13. For secretory phase data, the EM values did not fit a normal or lognormal distribution and so the statistical test of the null hypothesis that EM was not >NE was done using the non-parametric Wilcoxon rank sum test. The p value was 0.0083. As the EM and NE populations did not overlap, classifying NE data <20 pg/ml as negative and EM data >20 pg/ml as positive allowed use of Fisher's Exact test, an alternative non-parametric statistic, and the p value was 0.0061. The proliferative and menstrual EM and NE data did show a lognormal distribution, and the mean ln μ for 4 P NE cases was 3.75939±0.320341 compared to the ln μ for 5 P EM cases 3.69586±0.53613, and Student's t test value of 0.1017 with p=0.461. The rank sum p value for the null hypothesis that EM was not >NE was 0.500. For the menstrual cases, the mean ln μ for 3 NE cases was 4.00543±0.61168 and for 5 EM cases, 3.16278±0.38541, Student's t test value of 1.170 with p=0.143. The rank sum p for null hypothesis that M EM was not >M NE was p=0.197. P, proliferative; S, secretory; M, menstrual; NE, no endometriosis controls; EM, endometriosis cases. Thus. increased secretory phase sCD200 serum levels is associated with endometriosis.

The data was compared to another potential marker for endometriosis, namely, BDNF, and the results are shown in Table 5. Secretory phase plasma BDNF levels do not correlate with serum sCD200 levels. The result confirms serum CD200 to be a diagnostic marker of endometriosis.

TABLE 5

| EM Case # | BDNF value[a] | | sCD200 pg/ml ± 1 sem[b] | |
|---|---|---|---|---|
| No. 62 | 3,311.9 | POS | 53.37 ± 16.68 | POS |
| No. 85 | 461.0 | NEG | 1513.90 ± 312.80 | POS |
| No. 177 | 848.2 | NEG | 70.05 ± 10.01 | POS |
| No. 214 | 1,537.8 | POS | 60.04 ± 13.35 | POS |
| No. 225 | 822.1 | NEG | 173.64 ± 0 | POS |
| No. 205 | 70.8 | NEG | 57.15 ± 33.05 | POS[c] |

[a]data from Wessels et al. Fertil Steril 2016; 105: 119-28, BDNF > 999 is positive
[b]Based on duplicate wells (N = 2) at serum dilution of 1:2; sCD200 > 0 was positive as all non-EM controls were ≤ 10 pg/ml.
[c]neat was 120.7 ± 17.7 pg/ml. This serum was tested in a separate ELISA study where a neat serum sample was compared to a ½ dilution to assess prozone effects.

Example 3—CD200R1/CD200R2 Ratio in Secretory Phase EM Endometrial Tissue

Endometrial samples were retrieved via pipelle biopsy during surgery. Tissue samples were stabilized using RNAlater (Thermo Scientific, Mississauga, ON) and frozen until required for RNA analysis. Samples were weighed (30 mg) and placed into 700 μl of QIAzol Lysis Reagent (Qiagen, Toronto, ON) prior to homogenization (Bio-Gen, Oxford, Conn.). Total RNA was isolated from eutopic EM (n=17) and NE (n=8) endometrial samples, using the miRNeasy mini kit (Qiagen). Primers for all genes (CD200, CD200R1, CD200R2) were designed using Primer BLAST software available at the NCBI website. qRT-PCR reactions were carried out using forward and reverse primer sequences obtained from the McMaster University molecular biology core facility (Mobix, McMaster University) and as described previously. RNA was nano-dropped (Thermo Scientific) and reverse transcribed into cDNA using the iScript cDNA Synthesis Kit (BioRad, Mississauga, ON). Each qRT-PCR reaction consisted of 4 μl of 5×iScript reaction mix, 1 μl of iScript reverse transcriptase, and variable volumes of Nuclease-free water and RNA template to produce a cDNA volume of 200 ng. Each reaction was sequentially heated to 25° C. for 5 minutes, 42° C. for 30 minutes and 85° C. for 5 minutes. Real-time qPCR was performed using the CFX96 Touch Real-Time PCR Detection System (BioRad). Samples were analyzed in triplicate on a 384-well plate. Each well contained a reaction mixture including 2.5 μL of sample template cDNA, 1.5 μL RNAse-free water, 0.5 μL of the target forward and reverse primer and 5 uL of SYBR Green. Each 384-well plate was heated to 95° C. for 15 min, followed by 45 cycles at 94° C. for 10 seconds, 60° C. for 10 seconds and 72° C. for 10 seconds. This was followed by one cycle for melting curve acquisition.

Figure 14:
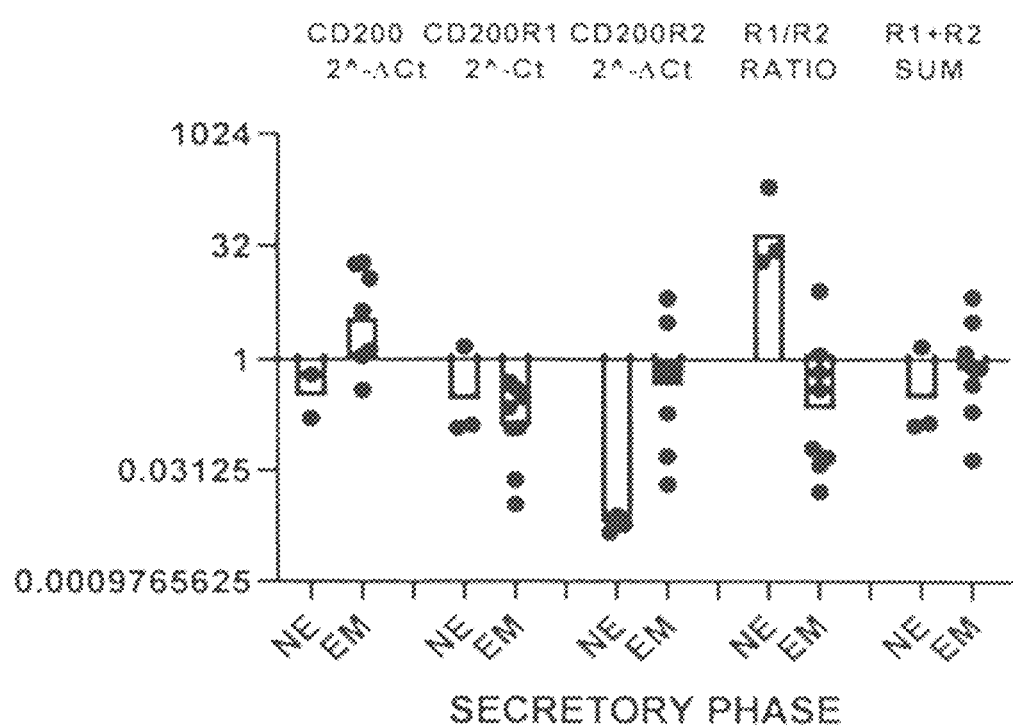
FIG. 14 provides a composite analysis using secretory phase data. Case specific ratios of CD200R1 and R2 levels together with the sum of CD200R1+CD200R2 for secretory phase patients are shown (A), and a pie diagram comparing the relative percentage of CD200R1+CD200R2 that was CD200R1 and CD200R2 comparing EM proliferative, secretory and menstrual cases to NE cases in the same menstrual cycle phase (B).
Figure 14:
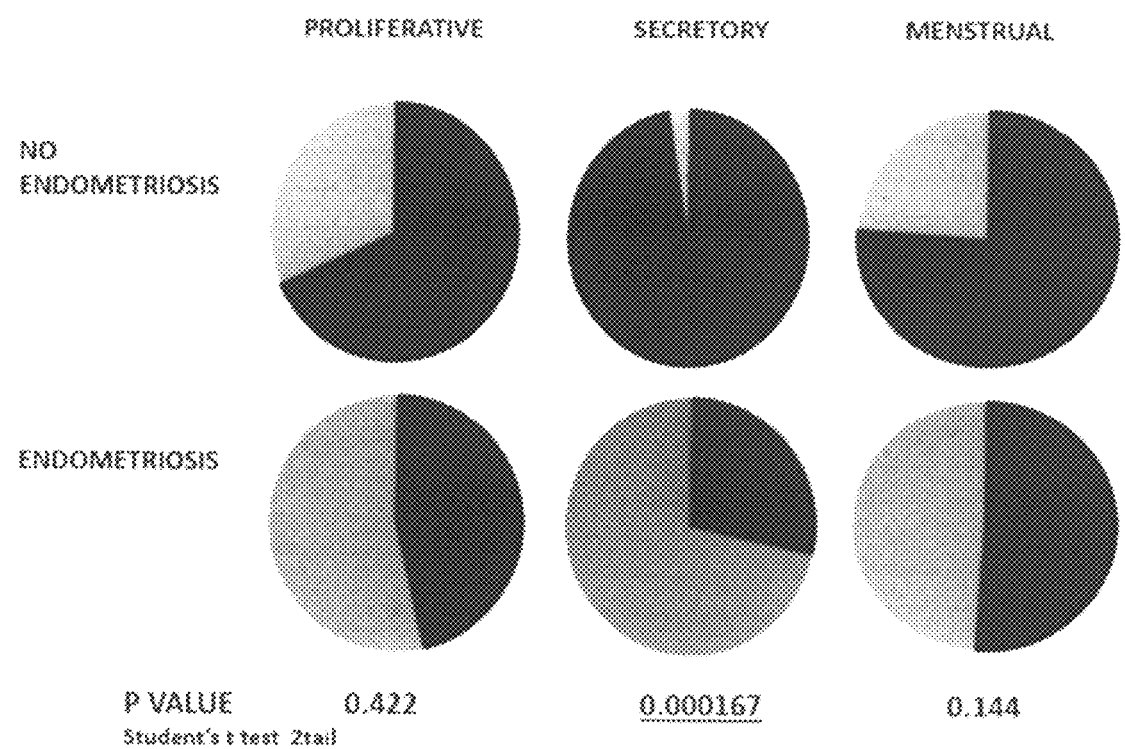

Results:

To determine if differences in serum sCD200 were related to differences in CD200 production in secretory phase EM cases, mRNA for CD200, CD200R1, and CD200R2 was determined by RT-PCR in 24 eutopic EM and NE endometrial samples but only three samples also had serum sCD200 measured, one secretory phase EM case, one proliferative phase NE, and one menstrual phase NE. In FIG. 14A, a total of eight EM and 3 NE secretory phase cases are shown, and in this group, only one EM case had had serum CD200 measured. CD200 mRNA expression was significantly greater for EM cases as the ln mean of 1.758±0.6618 was significantly greater than in NE where the ln mean value was −0.8308±0.5155 (FIG. 14A). Student's t test gave t=3.668 with p=0.0052, and the null hypothesis that CD200 mRNA was not increased in EM was therefore rejected. For CD200R1, the ln mean was −2.1134±0.4844 compared to the NE ln mean of −1.2638±0.8300. Student's t test gave t=0.904 for p=0.36 (2 tail) for the null hypothesis that CD200R1 was not increased or decreased. For CD200R2, however, the EM ln mean was −0.8390±0.6962 and the NE ln mean was −5.1286±0.1484, and Student's t was 2.860 with p=0.0188 for the null hypothesis of no difference. The null hypothesis of no difference was rejected. Therefore, increased synthesis of CD200 and CD200R2 was present in the secretory phase EM group compared to NE controls whereas a similar increase was not seen for CD200R1 mRNA levels. The ratio of $2^{-\Delta Ct}$ values in the NE and EM group individual cases also fit a lognormal distribution. In the NE group, the R1/R2 ratio ln mean±SEM was 3.3870±0.7063 compared to the EM group R1/R2 ratio ln mean of −1.5624±0.7556. This difference was statistically significant by Student's t test (t=3.038, 9 df, p=0.0141 2 tail) allowing the null hypothesis of no difference to be rejected and the alternative conclusion that the reduction in the R1/R2 ratio in EM was not likely due to chance to be accepted.

The ratio of CD200R1/CD200R2 mRNA was significantly reduced in the EM group compared to NE group. The change in ratio with CD200R1↓ and CD200R2↑ in EM proliferative phase samples as shown in FIG. 14A combined with CD200L and CD200S signaling can explain polarization of M2 macrophages that normally dominate in secretory phase endometrium to exhibit an M1 proinflammatory phenotype that is thought to be embryo-unfriendly and contribute to infertility (Vallve-Juanico et al., 2019).

FIG. 14B shows the % of CD200R that was CD200R1 and CD200R2 as a pie diagram for NE and EM cases in the proliferative, secretory, and menstrual phases of their cycle. The trend for CD200R to more CD200R1 than CD200R2 was evident in all phases of the cycle in EM eases but only achieved statistical significance in the secretory phase.

Example 4—IHC for CD200S

Anonymized tissue blocks from the initial IHC study of secretory phase hysterectomy samples (NE1, NE2, EM3, EM4, and EM5 described previously) and peritoneal endometrioma deposits were fixed in 10% buffered formalin for 24 hours at room temperature (22-23° C.), processed, and embedded in paraffin. Paraffin blocks were cut using a Leica CM2255 Microtome (Wetzlar, Germany) into 4 μm sections. Sections were affixed to positively charged slides and allowed to dry overnight at room temperature. Slides were dewaxed and hydrated on the automated Leica BOND Rx stain. Antigen retrieval was conducted using epitope retrieval buffer 2 (Leica). Slides were stained for CD200L using rabbit antigen-affinity purified antibody for AA 45-95 of the conical sequence (Antibodies Online ABIN761396), for CD200S using rabbit antigen-affinity purified antibodies for AA 170-220 (Antibodies-online, ABIN3189$^{6}$$^{6)}$, and rabbit anti-KLH antibody, also antigen-affinity purified (Antibodies-Online, ABIN401183), was used as a control. All antibodies were diluted 1:200 in Power Vision IHC Super Blocker (Leica) prior to staining. Slides were stained using the Bond Polymer Reline Detection kit (Leica). Slides were dehydrated, mounted in Fisher Chemical Permount Mounting Medium (Fisher Scientific, Hampton, N.H.) and digitally scanned and analyzed using Imagescope (Leica), and photographed at 200× and 400×.

Figure 15:
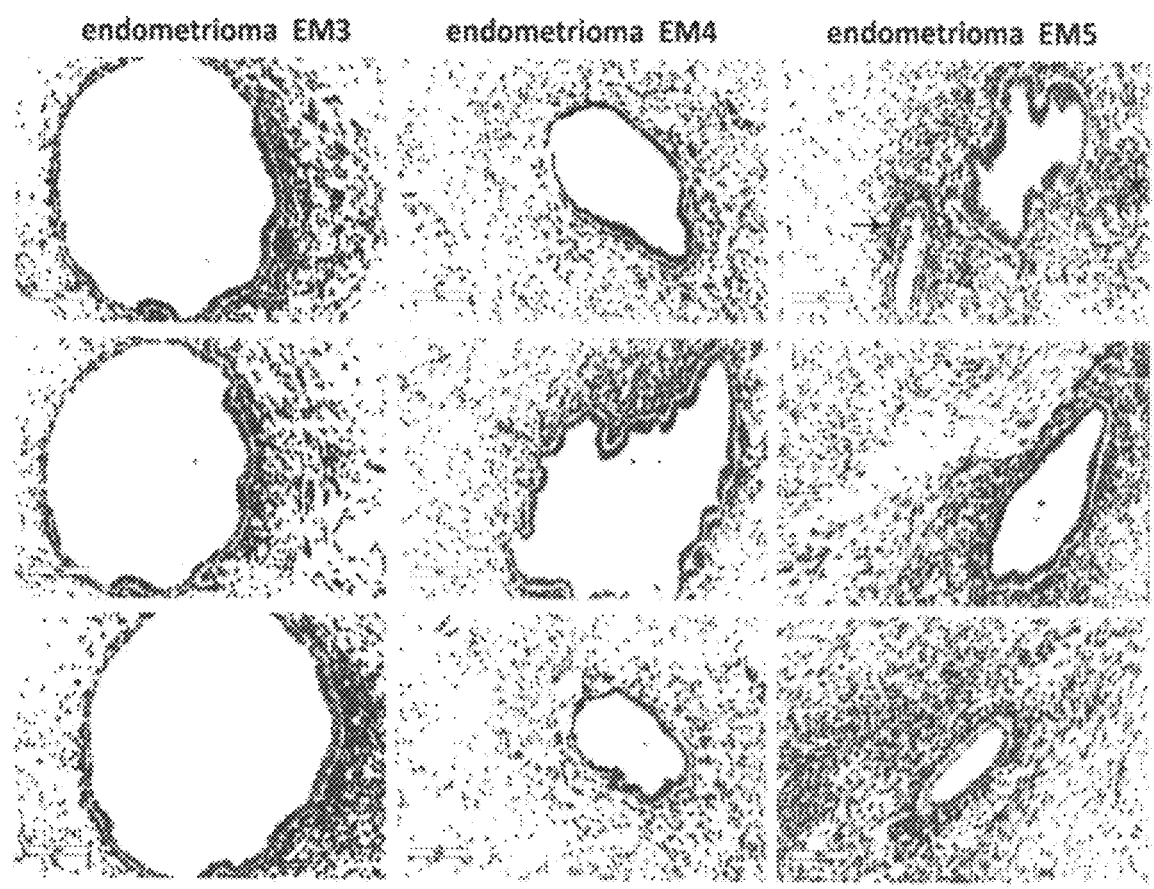
FIG. 15 provides photomicrographs (200× magnification—scale bar 100 nm) illustrating immunohistochemical staining of control (NE) and endometriosis (EM) secretory phase endometrium with CD200S antibody (A), immunohistochemical staining of peritoneal endometrioma deposits corresponding to the EM cases in FIG. 5(B), and immunohistochemical staining of endometriosis deposits found within the endometrium as adenomyosis (C).
Figure 15:
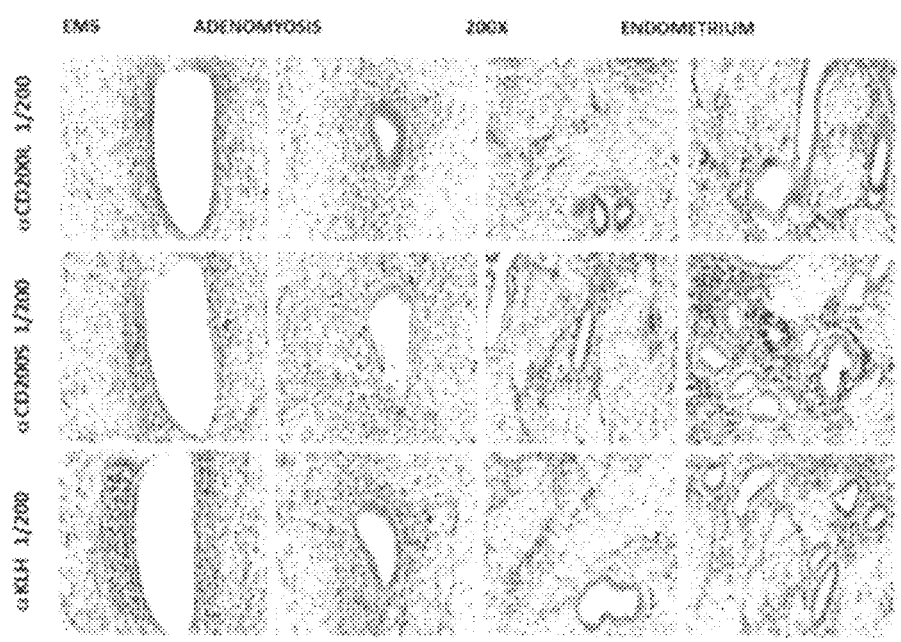

Results:

As shown in FIG. 15A, photomicrographs (200× magnification—scale bar 100 nm) illustrate immunohistochemical staining of control (NE) and endometriosis (EM) secretory phase endometrium with a 1/200 dilution of antibody to CD200S which reacts with Exon 4 determinants of CD200 variant 1 (amino acids (AA) 170-220). The staining indicates that this antibody does not react in our IHC procedure with full length CD200 (isoforms a and b), as access to AA 170-220 appears to be prevented by AA coded by Exon 2 and proximal Exon 3 AA. AA 170-220 become exposed when CD200 is truncated by elimination of exon 2 and proximal exon 3 AAs 32-73 of CD200 isoform a (variant 1) to form CD200S the transcription of which begins at AA 74 (M, methionine). This is compatible with CD200S being UniParc/UniProt F8W7G1. NM_001318826, NP_001305757 and distinct from the conventional longer molecule (CD200L).

To determine if there was a greater concentration of CD200S$^+$ cells in secretory phase EM endometrium, 11-13 photomicrographs done at 400× were evaluated as described above. The mean±SEM per unit volume (0.0335 mm$^3$ as described above) was NE1 26.0±2.2, NE2 57.8±8.1, EM3 67.9±11.5, EM4 80.5±8.8, EM5 83.6±6.5. and combining these results, NE was 41.3±5.1 and EM was greater at 77.4±4.8 with t=5.143 and p<0.01 (1 tail).* Scale bar 100 nm.

The photomicrographs of FIG. 15B illustrate immunohistochemical staining of peritoneal endometrioma deposits corresponding to the EM cases in FIG. 5 for presence of CD200S$^+$ leukocytes. In EM5, arrows point to a rare presence of positive cells. This contrasts with abundant CD200S$^+$ cells in the endometrium. Scale bar 100 nm.

Endometriosis deposits may also be found within the endometrium as adenomyosis as shown in FIG. 15C. Case EMS had adenomyosis and IHC result shows peri-myometrial and deep myometrial zones where CD200L$^+$ glandular epithelium and CD200S$^+$ cells in adjacent stroma/myometrium and basal endometrium where CD200l$^+$ glands which are intruding into the myometrium have been stained. This shows that CD200L and CD200S are clearly in different cells. Scale bar 100 nm. The photomicrograph shows that CD200S$^+$ cells were scant in the glandular deposit in myometrium.

The pattern of staining of CD200S$^+$ cells is compatible with them being uterine NK cells or a subset of NK cells. This was confirmed by cell comparison to the frequency of CD56$^+$ NK cells using a Leica mouse anti-CD56 antibody and a control antibody to CD68 on human macrophages (data not shown). CD200S in uNK cells has not previously been described. This discovery has implications for diagnosis of EM, if CD200S can be detected in serum by ELISA combined with elevated CD200L, that could predict likelihood that ongoing ectopic implants will occur with each menses. This provides evidence that anti-CD200S monoclonal antibody or an equivalent to block the initial inflammatory response required for implantation of ectopic tissue in combination with monoclonal anti-CD200L or an equivalent to abrogate suppression of the woman's immune system cells that are able to destroy ectopic tissue e.g. macrophages and NK cells.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

REFERENCES

Allan, S. E., Crome, D, Q., Crellin, N. K., Passerini, L., Steiner, T. B., Bacchetta, R., et al., 2007. Activation-induced FOXP3 in human T effector cells does not suppress proliferation or cytokine production. International Immunol. 19, 345-354.

Basta, P., Majka, M., Jozwicki, W., Lukaszewska, E., Knafel, A., Grabiec, M., et. al., 2010. The frequency of CD25+CD4+ and FOXP3+ regulatory T cells in ectopic endometrium and ectopic decidua. Reprod. Biol. Endocrinol. 8, 116.

Berbic, M., Hey-Cunningham, A. J., Ng, C., Tokushige, N., Ganewatta, S., Markham, R., et al., 2010. The role of Foxp3+ regulatory T-cells in endometriosis: a potential controlling mechanism for a complex chronic condition. Human Reprod. 25, 900-907.

Berbic, M., Fraser, I. S., 2011 Regulatory T cells and other leukocytes in the pathogenesis of endometriosis. J. Reprod. Immunol. 88, 149-155.

Bokor, A., Debrock, S., Drijkoningen, M., Goossens, W., Fulop, V., D'Hooghe, T. D., 2009. Quantity and quality of retrograde menstruation: a case control study. Reprod. Biol. Endocrinol. 7, 123.

Brosens, I., Brosens, J. J., Benagiano, G., 2012. The ectopic endometrium in endometriosis: are the changes of clinical significance? Reprod. Biomed. Online 24, 496-502.

Budiu, R. A., Diaconu, I., Chrissluis, R., Drici, A., Edwards, R. P., Vlad, A. M., 2000. A conditional mouse model for human MUC1-positive endometriosis shown the presence of anti-MUC1 antibodies and Foxp3+ regulatory T cells. Disease Models and Mechanisms 2, 593-603.

Clark, D. A., 2016a. The importance of being a regulatory T cell in pregnancy. J. Reprod. Immunol. 116: 60-69.

Clark, D. A., 2016b. Mouse is the new woman? Translational research in reproductive immunology. Seminars in Immunopathology 38, 651-668.

Clark, D. A., Gorczynski, R. M., 2013. Immunological tolerance/acceptance of the semiallogeneic embryo: decidual transforming growth factors and tolerance signaling molecules. In: G. Chaouat, G., Olivier, S., N Ledee, N. (Eds.), Immunology of Pregnancy 2013, Bentham eBooks (eISBN:978-1-60805-733-7), pp. 540-558.

Clark, D. A., Dmetrichuk, J. M., McCready, E., Dhesy-Thind, S., Arredondo, J. L., 2017. Changes in expression of the CD200 tolerance-signaling molecule and its receptor (CD200R1) by villus trophoblasts during first trimester misses abortion and in chronic histiocytic intervillositis. Am. J. Reprod. Immunol. 78e12665, 1-7.

Chen Z, Chen D-X, Kai Y, Khatri I, Lamptey B, Gorczynski R M. Identification of an expressed truncated form of CD200, CD200tr, which is a physiological antagonist of CD200-induced suppression. Transplantation 2008; 86:1116-1124.

Clement, P. B., 2007. The pathology of endometriosis. A survey of the many faces of a common disease emphasizing diagnostic pitfalls and unusual and newly appreciated aspects. Adv. Anat. Pathol. 14, 241-260.

Collette, T., Bellehumeur, C., Kats, R., Maheux, R., Maillous, J., Villeneuve, M., Akoum., 2004. Evidence for an increased release of proteolytic activity by eutopic endometrial tissue in women with endometriosis and for involvement of matric metaloproteinase-9. Human Reprod. 19, 1257-1264.

Dalbeth, N., Gundle, R., Davies, R. J., Lee, Y. C., McMichael, A. C., Callan, M. F., 2004. $CD56^{bright}$ NK cells are enriched at inflammatory sites and can engage with monocytes in a reciprocal program of activation. J. Immunol. 173, 6418-6426.

Ferreira, V. H., Dizzell, S., Nazli, A., Kalka, J. K., Mueller, K., Nguyen, P. V., et al., 2015. Medroxyprogesterone acetate regulates HIV-1 uptake and transcytosis but not replication in primary genital epithelial cells, resulting in enhanced T-cell infection. JID 211, 1745-1756.

Fraser, I. S., McCatton, G., Markham, R., Resta, T., Watts, A., 1986. Measured menstrual blood loss in women with menorrhagia associated with pelvic disease or coagulation disorders. Obstet. Gynaec. 61, 109-112.

Gargett, G. E., Schwab, K. E., Brosens, J. J., Puttemans, P., Benagiano, G., Brosens, I., 2014. Potential role of endometrial stem/progenitor cells in the pathogenesis of early-onset endometriosis. Molec. Hum. Reprod. 20, 591-598.

Gorczynski, R., Chen. Z., Kai, Y., Lee, L., Wong, S., Marsden, P. A., 2004. CD200 is a ligand for all members of the CD200R family of immunoregulatory molecules. J. Immunol., 172, 7744-7749.

Hatherley, D., Cherwinski, H. M., Moshref, M., Barclay, A. N., 2005. Recombinant CD200 protein does not bind activating proteins closely related to CD200 receptor. J. Immunol. 175, 2469-2474.

Jetten, N., Verbruggen, S., Gijbels, M. J., Post, M. J., De Winther M. P. J., Donners, M. M. P. C., 2014. Anti-inflammatory M2, but non pro-inflammatory M1 macrophages promote angiogenesis in vitro. Angiogenesis 17, 109-118.

Jones, R. K., Bulmer, J. N., Searle, R. F., 1996. Immunohistochemical characterization of stromal leukocytes in ovarian endometriosis: comparison of eutopic and ectopic endometrium with normal endometrium. Fertil. Steril. 66, 81-89.

Kohyashi K, Yano H, Umakoshi A. Matsumoto S, Mise A, Funahashi Y. Ueno Y, Kamei Y, Takada Y, Kumon Y, Olnishi T, Tanaka J. A truncated form of CD200 (CD200S) expression on glioma cells prolonged survival in a rat glioma model by induction of a dendritic cell-like phenotype in tumor associated macrophages. Neoplasia 2016; 18:229-241.

Kos, O., Hughson, R. L., Hart, D. A., Clement, G., Frings-Meuthen, P., Linnarsonm D., et al., 2014. Elevated serum soluble CD200 and CD200R as surrogate markers of bone loss under bed rest conditions. Bone 60, 33-40.

Kalu, E., Sumar, N., Giannopoulos, T., Patel, P., Croucher, C., Sherriff, E., et al., 2007. Cytokine profiles in serum and peritoneal fluid from infertile women with and without endometriosis. J. Obstet. Gynecol. Res. 33, 490-495.

Kaushic, C., Nazli, A., Ferreira, V. H., Kafka, J. K., 2011. Primary human epithelial cell culture system for studying interactions between female upper genital tract and sexually transmitted viruses, HSV-2 and HSV-1. Methods 55, 114-121.

Kruitwagen, R. F. P. M., Poels, L. G., Willemsen, W. N. P., de Ronde, I. J. Y., Jap, P. H. K., Roland, R., 1991. Endometrial epithelial cells in peritoneal fluid during the follicular phase. Fertil. Steril. 55, 297-303.

Li. M. Q., Wang, Y., Chang, K. K., Meng, Y. H., Liu, L. B., Mei, J., et al., 2014. CD4$^+$Foxp3$^+$ regulatory T cell differentiation mediated by an endometrial stromal-cell TECK promotes the growth and invasion of endometrial lesions. Cell Death & Disease 5, e14356.

Liu, K., Zhang, W., Liu, S., Dong, B., Liu, Y., 2015. Hepatic endometriosis: a rare case and review of the literature. Europ. J. Med. Res. 20, 48.

Luo, Q., Ning, W., Wu, Y., Zhu, X., Jin, F., Sheng, J., et al., 2006. Altered expression of interleukin-18 in the ectopic and eutopic endometrium of women with endometriosis. J. Reprod. Immunol. 72, 108-117.

Matsuzaki, S., Canis, M., Pouly, J. L., Botchorishvili, R., Deschelotte, P. J., Mage, G., 2006. Differential expression of genes in eutopic and ectopic endometrium from patients with ovarian endometriosis. Fertil. Steril. 86, 548-553.

Mbarik, M., Kaabachi, W., Henidi, B., Sassi, F. H., 2015. Soluble ST2 and IL-33: Potential markers of endometriosis in the Tunisian population. Immunol. Letters 166, 1-5.

Mei, J., Jin, L. P., Ding. D., Li, M. Q., Zhu, X. Y., 2012. Inhibition of IDO1 suppresses cycloxygenase-2 and matrix metalloproteinase-9 expression and decreases proliferation, adhesion and invasion of endometrial stromal cells. Molec. Human Reprod. 18, 467-476.

Mei. J., Li, M. Q., Ding, D., Li, D. J., Jin, L. P., Hu, W. G., Zhu, X. Y., 2013. Indoleamine 2,3-dioxygenase-1 (IDO1) enhances survival and invasiveness of endometrial stromal cells via the activation of the JNK signaling pathway. Int. J. Clin. Exp. Pathol. 6, 431-444.

Mei, J., Zhu, X Y., Jin, L P., Duan, Z L., Li, D J., Li, M-Q., 2015. Estrogen promotes the survival of human secretory phase endometrial stromal cells via CXCL12/CXCR4 up-regulation-mediated autophagy inhibition. Human Reprod. 30, 1677-1689.

Provinciali, M., Di Stefano, G., Muzzioli, M., Garzetti, G. G., Ciavattini, A., Fabris, N., 1995. Relationship between 17-β-estradiol and prolactin in the regulation of natural killer cell activity during progression of endometriosis. J. Endocrinol. Invest. 18, 645-652.

Ridley, J. H., Edwards, K., 1958. Experimental endometriosis in the human. Am. J. Obstet. Gynecol. 76, 783-789.

Scott, R. B., Te Linde, R. W., 1954. Further studies on experimental endometriosis. Am. J. Obstet. Gynecol. 66, 1082-1099.

Smith, K. A., Pearson, C. B., Hachey, A. M., Xia, D-L., Wachtman, L. M., 2012. Alternative activation of macrophages in rhesus macaques (Macaca mulatta) with endometriosis. Comparative Medicine 62, 303-310.

Somigliana, E., Vigano, P., Gaffuri, B., Candiani, M., Busacca, M., Di Blasio, A. M., et al., 1999. Modulation of NK cell lytic function by endometrial secretory factors: potential role in endometriosis. Am. J. Reprod. Immunol. 36, 295-300.

Somigliana, E., Candiana, M., Vignali, M., Vigano, P., 2001. Impaired natural killer cell activity in endometriosis?—A technical challenge for validation. Fertil. Steril. 76, 422.

Te Linde, R. W., Scott, R. B., 1950. Experimental endometriosis. Am. J. Obstet. Gynecol. 60, 1147-1166.

Tirado-Gonzalez, I., Barrientos, G., Tariverdian, N., Arck, P. C., Garcia, M. G., Klapp, B. F., et al., 2010. Endometriosis research: animal models for the study of a complex disease. J. Reprod. Immunol. 86, 141-147.

Treloar, S. A., O'Connor, D. T., O'Connor, V. M., Martin, N. G., 1999. Genetic influence on endometriosis in an Australian twin sample. Fertil Steril. 71, 701-710.

Vallve-Juanico J, Santamaria X, Vo K C, Houshdaran S, Giudice L C. Macrophages display proinflammatory phenotypes in the ectopic endometrium of women with endometriosis with relevance to an infectious etiology of the disease. Fertin Steril 2019; 112:1118-1128.

Vigano, P., Vercellini, P., Di Blasio, A. M., Colombo, A., Candiani, G. B., Vignali, M., 1991. Deficient antiendometrium lymphocyte-mediated cytotoxicity in patients with endometriosis. Fertil. Steril. 56, 894-899.

Vigano, P., Somigliana, E., Vignali, M., Busacca, M., Blasio, A. M., 2007. Genetics of endometriosis: current status and prospects. Front. Biosci. 12, 3247-3255

Wessels J M, Kay V R, Leyland N A, Agarwal S K, Foster W G. 2016. Assessing brain-derived neurotrophic Factor as a novel clinical markers in endometriosis. Fertil. Steril. 105:119-28.

Woidacki, K., Meyer, N., Schumacher, A., Goldschmidt, A., Maurer. N., Zenclussen, A. C., 2015. Transfer of regulatory T cells into abortion-prone mice promotes the expansion of uterine mast cells and normalizes early pregnancy angiogenesis. Sci. Rep. 5, 13938

Wolf, G. C., Singh, K. B., 1989. Caesarian scar endometriosis: a review. Obstet. Gynecol. Survey 44, 89-95.

Wong, K. K., Khatri, I., Shaha, S., Spanner, D. E., Gorczynski, R. M., 2010. The role fo CD200 in immunity to B cell lymphoma. J. Leuk. Biol. 88, 361-372

Wong, K. K., Brennerman, F., Chesney, A., Spaner, D. E., Gorczynsiki, R. M., 2012. Soluble CD200 is critical to engraft chronic lymphocytic leukemia cells in immunocompromised mice. Cancer Res. 72, 4931-4943.

Wong, K. K., Zhu, F., Khatri, I., Huo, Q., Spaner, D. E., Gorczynski, R. M., 2016. Characterization of CD200 ectodomain shedding. PLoS ONE 11, e0152073.

Wright, G. J., Cherwinski, H., Foster-Cuevas, M., Brooke, G., Puklavec, M. J., Bilger, M., et al., 2003. Characterization of the CD200 receptor family in mice and humans and their interaction with CD200. J. Immunol. 171, 3034-3046.

Wu, M., Yang. J., Chao, K., Hwang, J., Yang, Y., Ho, H., 2000. Increase in expression of killer inhibitory receptors on peritoneal natural killer cells in women with endometriosis. Fertil. Steril. 74, 1187-1191.

Xu, H., Zhang, T., Man, G. C. W., May, K. E., Becker, C. M., Davis, T. N., et al., 2013. Vascular endothelial growth factor C is increased in endometrium and promotes endothelial functions, vascular permeability and angiogenesis and growth of endometriosis, Angiogenesis 16, 541-551.

Yu, J. H., Lin, X. Y., Wang, L., Liu, Y., Fan, C. F., Zhang, Y., et al., 2013. Endobronchial endometriosis presenting as central-type lung cancer: a case report. Diagnostic Pathol. 8, 53.

Zamah, N. M., Dodson, M. G., Stephens, L. C., Buttram, V. C. Jr., Besch, P. G., Kaufman, R. H., 1984. Transplantation of normal and ectopic endometrial tissue into athymic nude mice. Am. J. Obstet. Gynecol. 149, 591-597.

The invention claimed is:

1. A method of diagnosing and treating endometriosis in a female subject, the method comprising:
   a) detecting levels of soluble and cellular CD200L in a menstrual secretory phase biological sample from the subject, wherein CD200L is detected using an antibody that binds to an exon region of exon 2 of CD200L that does not detect CD200S;
   b) comparing the level of CD200L in the biological sample with the level of CD200L in a control;
   c) diagnosing the subject with endometriosis when the level of CD200L in the biological sample is higher than the level of CD200L in the control; and
   d) treating the subject determined to have endometriosis with a treatment selected from administration of a nonsteroidal anti-inflammatory drug, an opioid, a hormone treatment that slows endometrial tissue growth and prevents new implants of endometrial tissue, gonadotropin-releasing hormone (GnRH) agonist, and a compound that inhibits the interaction of CD200L with CD200RI, and/or a compound that inhibits CD200S.

2. The method of claim 1, wherein the level of CD200L is detected using an immunoassay utilizing an antibody that targets an antigen in CD200L encoded by the exon region.

3. The method of claim 1, including an additional step of detecting the level of CD200S in the sample to determine a ratio of CD200L to CD200S, wherein the ratio of CD200L to CD200S which is greater than 1 is indicative of endometriosis.

4. The method of claim 3, wherein levels of CD200S is detected by detecting levels of CD200L+CD200S using an antibody raised against amino acids encoded by exon 3 of CD200L.

5. A method of diagnosing and treating endometriosis in a female subject, the method comprising:
   a) detecting levels of soluble and cellular CD200L in a menstrual secretory phase biological sample from the subject, wherein CD200L is detected using an antibody that binds to an exon region of exon 2 of CD200L that does not detect CD200S;
   b) detecting levels of CD200S in the biological sample;
   c) comparing levels of CD200L in the biological sample with the level of CD200S; and diagnosing the subject with endometriosis when the level of CD200L in the biological sample is higher than the level of CD200S in the sample; and
   d) treating the subject determined to have endometriosis with a treatment selected from administration of a nonsteroidal anti-inflammatory drug, an opioid, a hormone treatment that slows endometrial tissue growth and prevents new implants of endometrial tissue, a gonadotropin-releasing hormone (GnRH) agonist, and a compound that inhibits the interaction of CD200L with CD200RI, and/or a compound that inhibits CD200S.

* * * * *